United States Patent
Furuya et al.

(10) Patent No.: US 11,920,335 B2
(45) Date of Patent: Mar. 5, 2024

(54) INFORMATION PROCESSING SYSTEM, INFORMATION PROCESSING APPARATUS, INFORMATION PROCESSING METHOD, AND NON-TRANSITORY COMPUTER-READABLE MEDIUM

(71) Applicant: NEC Platforms, Ltd., Kawasaki (JP)

(72) Inventors: Satoshi Furuya, Kanagawa (JP); Tsutomu Mieno, Kanagawa (JP); Haruhiko Yamabuchi, Kanagawa (JP)

(73) Assignee: NEC Platforms, Ltd., Kanagawa (JP)

( * ) Notice: Subject to any disclaimer, the term of this patent is extended or adjusted under 35 U.S.C. 154(b) by 226 days.

(21) Appl. No.: 17/632,312

(22) PCT Filed: May 27, 2020

(86) PCT No.: PCT/JP2020/020964
§ 371 (c)(1),
(2) Date: Feb. 2, 2022

(87) PCT Pub. No.: WO2021/024584
PCT Pub. Date: Feb. 11, 2021

(65) Prior Publication Data
US 2022/0333364 A1   Oct. 20, 2022

(30) Foreign Application Priority Data
Aug. 8, 2019   (JP) .................................. 2019-146294

(51) Int. Cl.
*E03D 9/00* (2006.01)
*E03D 5/10* (2006.01)
(Continued)

(52) U.S. Cl.
CPC .............. *E03D 9/002* (2013.01); *E03D 5/10* (2013.01); *G06T 7/0002* (2013.01); *G06V 40/172* (2022.01)

(58) Field of Classification Search
CPC .. E03D 9/002; E03D 5/10; E03D 9/00; G06T 7/0002; G06V 40/172; G16H 30/40;
(Continued)

(56) References Cited

U.S. PATENT DOCUMENTS

2010/0134300 A1   6/2010   Fukai
2010/0146691 A1   6/2010   Chan
(Continued)

FOREIGN PATENT DOCUMENTS

CN   108685584 A   10/2018
CN   109464158 A   3/2019
(Continued)

OTHER PUBLICATIONS

Taiwanese Office Action for TW Application No. 109119458 dated Apr. 28, 2022 with English Translation.
(Continued)

*Primary Examiner* — Lori L Baker
(74) *Attorney, Agent, or Firm* — Sughrue Mion, PLLC

(57) ABSTRACT

An information processing system includes an acquisition unit that acquires excretion information, based on imaging data captured by an image capture apparatus installed in such a way as to include, in an image capture range, an excretion range of excrement in a toilet bowl of a toilet, a generation unit that generates presentation information to be output, based on the excretion information, and a control unit. The acquisition unit acquires information that indicates whether a foreign body being an object other than feces and urine is included in the imaging data as a subject excluding the toilet bowl and washing liquid for the toilet bowl. When information including the foreign body is acquired, the control unit outputs a stop command for stopping a washing function of the toilet bowl to the toilet bowl side, and the
(Continued)

generation unit generates alert information as at least a part of the presentation information.

15 Claims, 20 Drawing Sheets

(51) Int. Cl.
  *G06T 7/00* (2017.01)
  *G06V 40/16* (2022.01)
(58) Field of Classification Search
  CPC ........ G16H 40/67; G16H 50/20; G16H 40/60; A61G 9/00; A61G 2203/30; A61G 12/00; G08B 23/00; G08B 21/02; G08B 25/04; G01N 33/50; G01N 33/483; A47K 17/00; A47K 2017/006
  USPC .............................................. 4/662; 700/282
  See application file for complete search history.

(56) References Cited

U.S. PATENT DOCUMENTS

| | | |
|---|---|---|
| 2017/0370936 A1 | 12/2017 | Hasegawa et al. |
| 2018/0087969 A1 | 3/2018 | Hall et al. |
| 2023/0156439 A1* | 5/2023 | Mayer .................. G06F 3/0482 134/18 |

FOREIGN PATENT DOCUMENTS

| | | |
|---|---|---|
| JP | H05-228181 A | 9/1993 |
| JP | H07-119190 A | 5/1995 |
| JP | H08-052097 A | 2/1996 |
| JP | 2006-225966 A | 8/2006 |
| JP | 2010-220761 A | 10/2010 |
| JP | 2012-507646 A | 3/2012 |
| JP | 2016-145808 A | 8/2016 |
| JP | 2017-004320 A | 1/2017 |
| JP | 2018-029237 A | 2/2018 |
| TW | 201904533 A | 2/2019 |
| WO | 2009/016727 A1 | 2/2009 |
| WO | WO-2018005445 A1 * | 1/2018 ........... A61K 31/436 |

OTHER PUBLICATIONS

Japanese Office Communication for JP Application No. 2021-537590 dated Nov. 8, 2022 with English Translation.
International Search Report for PCT Application No. PCT/JP2020/020964, dated Aug. 18, 2020.

* cited by examiner

| INFORMATION TO BE RECORDED | CONTENT |
|---|---|
| DATE AND TIME OF OCCURRENCE | DATE AND TIME |
| TARGET PERSON | PERSONAL NAME OF CARE RECEIVER |
| PLACE OF OCCURRENCE | FACILITY NAME, TOILET NAME |
| TYPE OF EXCREMENT | DEFECATION or URINATION or FOREIGN BODY |
| AMOUNT OF URINATION | MANY or NORMAL or FEW |
| SHAPE OF DEFECATION | HARD or NORMAL or DIARRHEA |
| COLOR OF DEFECATION | WRITE COLOR |
| NUMBER OF TIMES | URINATION AND EXCRETION COUNT |
| SPECIAL NOTES | MANUAL INPUT FIELD |

Fig. 11

| HOUR | MINUTE :SECOND | [Mr. PA] | | | | | | | |
|---|---|---|---|---|---|---|---|---|---|
| | | FACILITY NAME | TYPE | AMOUNT | SHAPE | COLOR | EXCRETION COUNT | CAREGIVER NAME | SPECIAL NOTES |
| 0 | | | | | | | | | |
| 1 | | | | | | | | | |
| 2 | | | | | | | | | |
| 3 | | | | | | | | | |
| 4 | | | | | | | | | |
| 5 | | | | | | | | | |
| 6 | 24:30 | 4F MEN'S TOILET 01 | FECES | | | | 2 | CAREGIVER CA | |
| | 30:12 | 4F MEN'S TOILET 02 | URINE | | | | 4 | CAREGIVER CA | |
| 7 | | | | | | | | | |
| 8 | | | | | | | | | |
| 9 | | | | | | | | | |
| 10 | | | | | | | | | |
| 11 | | | | | | | | | |
| 12 | | | | | | | | | |
| 13 | | | | | | | | | |
| 14 | | | | | | | | | |
| 15 | | | | | | | | | |
| 16 | | DIAPER | URINE | 30 | | YELLOW | 1 | CAREGIVER CB | MANUAL |
| 17 | | | | | | | | | |
| 18 | | | | | | | | | |
| 19 | | | | | | | | | |
| 20 | | | | | | | | | |
| 21 | | | | | | | | | |
| 22 | | | | | | | | | |
| 23 | | | | | | | | | |
| SUM | | | FECES | — | — | 2 | | | |
| | | | URINE | — | — | 5 | | | |

| HOUR | 2020/1/1 (WEDNESDAY) | | | | | | 2020/1/2 (THURSDAY) | | | | | | 2020/1/3 (FRIDAY) | | | | | |
|---|---|---|---|---|---|---|---|---|---|---|---|---|---|---|---|---|---|---|
| | TYPE | AMOUNT | SHAPE | CO-LOR | EXCRE-TION COUNT | SPE-CIAL NOTES | TYPE | AMOUNT | SHAPE | CO-LOR | EXCRE-TION COUNT | SPE-CIAL NOTES | TYPE | AMOUNT | SHAPE | CO-LOR | EXCRE-TION COUNT | SPE-CIAL NOTES |
| 0 | | | | | | | | | | | | | | | | | | |
| 1 | | | | | | | | | | | | | | | | | | |
| 2 | URINE | 30 | | YELLOW | 1 | MANUAL | | | | | | | | | | | | |
| 3 | | | | | | | | | | | | | | | | | | |
| 4 | | | | | | | | | | | | | | | | | | |
| 5 | | | | | | | | | | | | | | | | | | |
| 6 | FECES / URINE | | | | 2 / 4 | | | | | | | | FECES / URINE | | | | 2 / 4 | |
| 7 | | | | | | | | | | | | | | | | | | |
| 8 | | | | | | | | | | | | | | | | | | |
| 9 | | | | | | | | | | | | | | | | | | |
| 10 | | | | | | | | | | | | | | | | | | |
| 11 | | | | | | | | | | | | | | | | | | |
| 12 | | | | | | | URINE | | | | 1 | | | | | | | |
| 13 | | | | | | | | | | | | | | | | | | |
| 14 | | | | | | | | | | | | | | | | | | |
| 15 | | | | | | | | | | | | | | | | | | |
| 16 | | | | | | | URINE | 30 | | YELLOW | 1 | MANUAL | | | | | | |
| 17 | | | | | | | | | | | | | | | | | | |
| 18 | | | | | | | | | | | | | | | | | | |
| 19 | | | | | | | | | | | | | | | | | | |
| 20 | | | | | | | | | | | | | URINE | 30 | | YELLOW | 1 | MANUAL |
| 21 | | | | | | | | | | | | | | | | | | |
| 22 | | | | | | | | | | | | | | | | | | |
| 23 | | | | | | | | | | | | | | | | | | |
| SUM | FECES / URINE | | | — / — | — / — | 2 / 5 | FECES / URINE | | | — / — | — / — | -1 / 2 | FECES / URINE | | | — / — | — / — | 2 / 5 |

Fig. 13

| 2020/1/4 (SATURDAY) | | | | | | 2020/1/5 (SUNDAY) | | | | | |
|---|---|---|---|---|---|---|---|---|---|---|---|
| TYPE | AMOUNT | SHAPE | COLOR | EXCRE-TION COUNT | SPECIAL NOTES | TYPE | AMOUNT | SHAPE | COLOR | EXCRE-TION COUNT | SPECIAL NOTES |
| | | | | | | | | | | | |
| | | | | | | | | | | | |
| | | | | | | | | | | | |
| | | | | | | | | | | | |
| | | | | | | | | | | | |
| | | | | | | | | | | | |
| | | | | | | | | | | | |
| | | | | | | | | | | | |
| | | | | | | | | | | | |
| | | | | | | | | | | | |
| URINE | | | | 1 | | | | | | | |
| | | | | | | | | | | | |
| | | | | | | | | | | | |
| URINE | | | | 1 | | | | | | | |
| URINE | | | | 1 | | | | | | | |
| | | | | | | | | | | | |
| | | | | | | | | | | | |
| URINE | | | | 1 | | | | | | | |
| | | | | | | URINE | | | | 1 | |
| | | | | | | | | | | | |
| | | | | | | | | | | | |
| | | | | | | | | | | | |
| | | | | | | | | | | | |
| | | | | | | | | | | | |
| | | | | | | URINE | 30 | | YELLOW | 1 | MANUAL |
| | | | | | | | | | | | |
| | | | | | | | | | | | |
| | | | | | | | | | | | |
| | | | | | | | | | | | |
| | | | | | | | | | | | |
| | | | | | | | | | | | |
| | | | | | | | | | | | |
| | | | | | | | | | | | |
| | | | | | | | | | | | |
| FECES | — | — | | −1 | | FECES | — | — | | −2 | |
| URINE | — | — | | 4 | | URINE | — | — | | 2 | |

Fig. 14

2020/1/1 (WEDNESDAY)

| HOUR | Mr. PA | | | | | | Mr. PB | | | | | | MR. PC | | | | | |
|---|---|---|---|---|---|---|---|---|---|---|---|---|---|---|---|---|---|---|
| | TYPE | AMOUNT | SHAPE | CO-LOR | EXCRE-TION COUNT | SPE-CIAL NOTES | TYPE | AMOUNT | SHAPE | CO-LOR | EXCRE-TION COUNT | SPE-CIAL NOTES | TYPE | AMOUNT | SHAPE | CO-LOR | EXCRE-TION COUNT | SPE-CIAL NOTES |
| 0 | | | | | | | | | | | | | | | | | | |
| 1 | | | | | | | | | | | | | | | | | | |
| 2 | URINE | 30 | | YELLOW | 1 | MANUAL | | | | | | | | | | | | |
| 3 | | | | | | | | | | | | | | | | | | |
| 4 | | | | | | | | | | | | | | | | | | |
| 5 | | | | | | | | | | | | | | | | | | |
| 6 | FECES | | | | 2 | | | | | | | | FECES | | | | 2 | |
| | URINE | | | | 4 | | | | | | | | URINE | | | | 4 | |
| 7 | | | | | | | | | | | | | | | | | | |
| 8 | | | | | | | | | | | | | | | | | | |
| 9 | | | | | | | | | | | | | | | | | | |
| 10 | | | | | | | | | | | | | | | | | | |
| 11 | | | | | | | | | | | | | | | | | | |
| 12 | | | | | | | URINE | | | | 1 | | | | | | | |
| 13 | | | | | | | | | | | | | | | | | | |
| 14 | | | | | | | | | | | | | | | | | | |
| 15 | | | | | | | | | | | | | | | | | | |
| 16 | | | | | | | URINE | 30 | | YELLOW | 1 | MANUAL | | | | | | |
| 17 | | | | | | | | | | | | | | | | | | |
| 18 | | | | | | | | | | | | | | | | | | |
| 19 | | | | | | | | | | | | | | | | | | |
| 20 | | | | | | | | | | | | | URINE | 30 | | YELLOW | 1 | MANUAL |
| 21 | | | | | | | | | | | | | | | | | | |
| 22 | | | | | | | | | | | | | | | | | | |
| 23 | | | | | | | | | | | | | | | | | | |
| SUM | FECES | | — | — | 2 | | FECES | | — | — | −1 | | FECES | | — | — | 2 | |
| | URINE | | — | — | 5 | | URINE | | — | — | 2 | | URINE | | — | — | 5 | |

Fig. 15

INFORMATION PROCESSING SYSTEM, INFORMATION PROCESSING APPARATUS, INFORMATION PROCESSING METHOD, AND NON-TRANSITORY COMPUTER-READABLE MEDIUM

This application is a National Stage Entry of PCT/JP2020/020964 filed on May 27, 2020, which claims priority from Japanese Patent Application 2019-146294 filed on Aug. 8, 2019, the contents of all of which are incorporated herein by reference, in their entirety.

TECHNICAL FIELD

The present disclosure relates to an information processing system, an information processing apparatus, an information processing method, and a program.

BACKGROUND ART

A caregiver, who provides excretion assistance at a caregiving site, is required to reduce incontinence of a care receiver and support independence of the care receiver while maintaining dignity of the care receiver. Since the excretion assistance at a caregiving site may damage dignity of the care receiver according to occasions, a caregiver is forced to bear a heavy burden, and support for reducing a load of work is required.

The work of the caregiver also includes work of making an excretion diary in excretion assistance of the care receiver. Therefore, the caregiver obtains information to be written in the excretion diary by entering a toilet with a care receiver and observing an excretion behavior of the care receiver, or hearing from the care receiver.

The former is mainly performed for a care receiver from whom accurate information is not heard due to dementia and the like. In the former case, since observing an excretion behavior is a shame for the care receiver, it can be said that dignity of the care receiver is likely to be damaged, and observation in such a scene is a task that imposes a burden on the caregiver. Meanwhile, in the latter case, since an inaccurate application may occur due to a sense of shame of a care receiver, it can be said that there is personality in excretion record, and as a consequence, even though the care receiver performs the same excretion behavior, a difference may occur in a content of an excretion diary. Thus, accuracy of an excretion diary made by hearing may be low while the burden of the caregiver is heavy.

Furthermore, when a care receiver has dementia, the care receiver mistakes a urine absorbing pad as a toilet paper during excretion or intentionally tries to hide an evidence of excretion failure (incontinence of feces and urine) due to his/her shame, thereby the urine absorbing pad may be flushed to the toilet. In such a case or on a regular basis, a care facility asks a contractor to perform drain pipe cleaning work, such as foreign body removal, in order to clear clogging of a drain pipe, and furthermore it is not possible to operate a drainage-related facility during the work.

In relation to recording of the number of uses of a toilet, Patent Literature 1 discloses an apparatus for generating information for safety determination, which detects a use of a toilet by a monitored person by using a contact sensor in a flush operation unit, and transmits device use information representing the use of the toilet, to a remote monitoring apparatus as safety determination information. The apparatus for generating information for safety determination can store a threshold for the number of uses of the toilet per day, and display a warning message, such as "the number of excretion behaviors is abnormal", on condition that the number of uses per day exceeds the threshold.

Patent Literature 2 discloses a system including a subject-side apparatus installed in a toilet room and a server communicable with the subject-side apparatus. The subject-side apparatus includes a sulfur-containing gas sensor configured to respond to sulfur-containing gas and output detection data, and a transceiver for transmitting, to a server, measurement data including the detection data of sulfur-containing gas detected by the sulfur-containing gas sensor. The server includes a database configured to cumulatively record the measurement data including the detection data of the sulfur-containing gas detected by the sulfur-containing gas sensor together with a date and time of defecation in association with subject identification information. Furthermore, the server includes a server-side data analysis means for analyzing physical health of a subject, based on a temporal variation trend of the measurement data cumulatively recorded in the database. Furthermore, the system disclosed in Patent Literature 2 can also be provided with an input apparatus that receives input of defecation history information, whereby a doctor and the like can accurately diagnose whether the subject has constipation, based on the analysis result of the measurement data and the defecation history information.

Patent Literature 3 discloses a system that detects an excretion behavior on the basis of a human body detection signal from a human detecting sensor installed in a toilet, stores a schedule of excretion behaviors, and notifies forgetting of an excretion behavior when an excretion behavior is not detected at a scheduled time.

Patent Literature 4 discloses a toilet bowl with an alarm apparatus, which includes a sensor for detecting a sitting state of a user onto a toilet seat, a timer starting an operation on the basis of a signal from the sensor, and an alarming means for emitting an alarm on the basis of an output signal of the timer after the operation of a prescribed time. The toilet bowl with the alarm apparatus can detect and notify that a user has been sitting for a long time, and may also be configured to notify a nurse station of such an abnormal state.

Patent Literature 5 discloses a water closet including a toilet bowl, a judgment unit, and a water supply control unit. In the water closet, the judgment unit judges whether to be feces or urine on the basis of a detection result of an $H_2S$ sensor, and the water supply control unit controls an amount of water supply for feces or urine on the basis of the judgment result. Patent Literature 5 also discloses that the judgment unit judges presence or absence of a foreign body (feces, a toilet paper core, and the like) in stagnant water of the toilet bowl on the basis of a result acquired by visual detection of a vision sensor element, or on the basis of a result acquired by optical detection of a light emitting element and a light receiving element.

CITATION LIST

Patent Literature

Patent Literature 1: International Patent Publication No. WO2009/016727
Patent Literature 2: Japanese Unexamined Patent Application Publication No. 2016-145808
Patent Literature 3: Japanese Unexamined Patent Application Publication No. 2010-220761

Patent Literature 4: Japanese Unexamined Patent Application Publication No. H08-052097

Patent Literature 5: Japanese Unexamined Patent Application Publication No. H07-119190

SUMMARY OF INVENTION

Technical Problem

However, since a main purpose of the technology disclosed in Patent Literature 1 is safety determination, it is only possible to determine the number of excretion behaviors, thus it is not possible to acquire information indicating a content of excretion being required for an excretion diary. Furthermore, since the technology disclosed in Patent Literature 2 uses a sulfur-containing gas sensor, it is not possible to determine physical health of a subject on the basis of appearance of excrement, and questions to the subject and manual input are required in order to acquire defecation history information.

Furthermore, the technologies disclosed in Patent Literatures 3 and 4 can notify forgetting to excrete and sitting for a long time by a user, respectively, but are not able to acquire information indicating the content of excretion behavior being required for an excretion diary.

Moreover, even when a foreign body other than excrement is present in a toilet bowl, the technologies disclosed in Patent Literatures 1 to 4 are not able to detect the foreign body, and to inspect the foreign body because a user may flush the foreign body.

Furthermore, the technology disclosed in Patent Literature 5 only detects presence or absence of a foreign body, and since feces is included in the foreign body to be detected, the technology is not able to distinguish between excrement and other substances for detection. Moreover, in the technology disclosed in Patent Literature 5, for example, even though a toilet paper core is detected, an amount of water supply is controlled to an appropriate amount that does not cause a residue, and it is not considered to stop water supply. Thus, in the technology disclosed in Patent Literature 5, for example, even when a foreign body, such as hematemesis or vomit, is present in stagnant water of a toilet bowl, since a user may flush the foreign body, it is not possible to inspect the foreign body.

An object of the present disclosure is to provide an information processing system, an information processing apparatus, an information processing method, and a program that solve the aforementioned issue. The above issue is to collect excretion information indicating a content of excrement in a toilet bowl without having to ask a user of a toilet and prevent flushing of a foreign body other than the excrement, even when the foreign body is present in the toilet bowl.

Solution to Problem

An information processing system according to a first aspect of the present disclosure includes: an acquisition unit that acquires excretion information indicating a content of excretion on the basis of imaging data captured by an image capture apparatus installed in such a way as to include, in an image capture range, an excretion range of excrement in a toilet bowl of a toilet; a generation unit that generates presentation information on the basis of the excretion information; an output unit that outputs the presentation information; and a washing control unit that controls a washing function of the toilet bowl, wherein the acquisition unit acquires information that indicates whether a foreign body being an object other than feces and urine is included in the imaging data captured by the image capture apparatus as a subject excluding the toilet bowl and washing liquid for the toilet bowl, as at least a part of the excretion information, the washing control unit outputs a stop command for stopping the washing function to a side of the toilet bowl when the acquisition unit acquires information including the foreign body as the excretion information, and the generation unit generates alert information as at least a part of the presentation information when the acquisition unit acquires the information including the foreign body as the excretion information.

An information processing apparatus according to a second aspect of the present disclosure is an information processing apparatus including an image capture apparatus and being installed on a toilet bowl of a toilet in such a way that the image capture apparatus is disposed in such a way as to include, in an image capture range, an excretion range of excrement in the toilet bowl, and further includes: an acquisition unit that acquires excretion information indicating a content of excretion on the basis of imaging data captured by the image capture apparatus; a generation unit that generates presentation information on the basis of the excretion information; an output unit that outputs the presentation information; and a washing control unit that controls a washing function of the toilet bowl, wherein the acquisition unit acquires information that indicates whether a foreign body being an object other than feces and urine is included in the imaging data captured by the image capture apparatus as a subject excluding the toilet bowl and washing liquid for the toilet bowl, as at least a part of the excretion information, the washing control unit outputs a stop command for stopping the washing function to a side of the toilet bowl when the acquisition unit acquires information including the foreign body as the excretion information, and the generation unit generates alert information as at least a part of the presentation information when the acquisition unit acquires the information including the foreign body as the excretion information.

An information processing method according to a third aspect of the present disclosure includes: an acquisition step of acquiring excretion information indicating a content of excretion on the basis of imaging data captured by an image capture apparatus installed in such a way as to include, in an image capture range, an excretion range of excrement in a toilet bowl of a toilet; a generation step of generating presentation information on the basis of the excretion information; an output step of outputting the presentation information; and a washing control step of controlling a washing function of the toilet bowl, wherein: in the acquisition step, information that indicates whether a foreign body being an object other than feces and urine is included in the imaging data captured by the image capture apparatus as a subject excluding the toilet bowl and washing liquid for the toilet bowl, is acquired as at least a part of the excretion information; in the washing control step, when information including the foreign body is acquired as the excretion information in the acquisition step, a stop command for stopping the washing function is output to a side of the toilet bowl; and in the generation step, when the information including the foreign body is acquired as the excretion information in the acquisition step, alert information is generated as at least a part of the presentation information.

A program according to a fourth aspect of the present disclosure causes a computer to perform: an acquisition step of acquiring excretion information indicating a content of excretion on the basis of imaging data captured by an image capture apparatus installed in such a way as to include, in an image capture range, an excretion range of excrement in a toilet bowl of a toilet; a generation step of generating presentation information on the basis of the excretion information; an output step of outputting the presentation information; and a washing control step of controlling a washing function of the toilet bowl, wherein: in the acquisition step, information that indicates whether a foreign body being an object other than feces and urine is included in the imaging data captured by the image capture apparatus as a subject excluding the toilet bowl and washing liquid for the toilet bowl, is acquired as at least a part of the excretion information; in the washing control step, when information including the foreign body is acquired as the excretion information in the acquisition step, a stop command for stopping the washing function is output to a side of the toilet bowl; and in the generation step, when the information including the foreign body is acquired as the excretion information in the acquisition step, alert information is generated as at least a part of the presentation information.

Advantageous Effects of Invention

The present disclosure is able to provide an information processing system, an information processing apparatus, an information processing method, and a program that solve the aforementioned issue. Specifically, according to the present disclosure, it is possible to collect excretion information indicating a content of excrement in a toilet bowl without having to ask a user of a toilet and prevent flushing of a foreign body other than the excrement, even when the foreign body is present in the toilet bowl.

BRIEF DESCRIPTION OF DRAWINGS

FIG. 11 is a diagram illustrating an example of information recorded in the information processing system in FIG. 2 or FIG. 10.

FIG. 12 is a diagram illustrating an example of a daily excretion diary for a certain person, which is generated in the information processing system in FIG. 2 or FIG. 10.

FIG. 13 is a diagram illustrating an example of an excretion diary for a certain person, which is generated in the information processing system in FIG. 2 or FIG. 10.

FIG. 14 is a diagram illustrating a continuation of the excretion diary in FIG. 13.

FIG. 15 is a diagram illustrating an example of a daily excretion diary for a plurality of persons, which is generated in the information processing system in FIG. 2 or FIG. 10.

DESCRIPTION OF EMBODIMENTS

Figure 1:
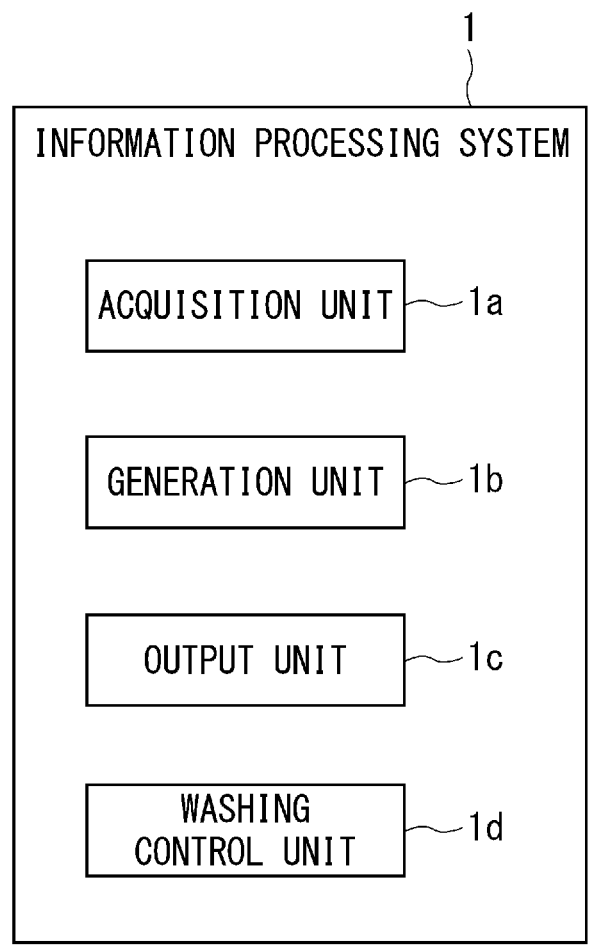
FIG. 1 is a block diagram illustrating a configuration example of an information processing system according to a first example embodiment.

Hereinafter, example embodiments will be described with reference to the drawings. In the example embodiments, the same or equivalent elements are given the same reference numerals and redundant description thereof will be omitted.

First Example Embodiment

FIG. 1 is a block diagram illustrating a configuration example of an information processing system according to a first example embodiment.

As illustrated in FIG. 1, an information processing system 1 according to the present example embodiment may include an acquisition unit 1a, a generation unit 1b, an output unit 1c, and a washing control unit 1d.

The acquisition unit 1a acquires excretion information indicating the content of excretion on the basis of imaging data captured by an image capture apparatus (hereinafter, exemplified as a camera) installed to include in an image capture range an excretion range of excrement in a toilet bowl of a toilet. Therefore, the information processing system 1 is connected to or includes the camera installed in this way. The camera is not limited to a visible light camera, and may be an infrared light camera and the like, and may also be a video camera as long as a still image can be extracted.

The above excretion range can be an area including a stagnant part of the toilet bowl, and can also be referred to as a scheduled excretion range. By installing the camera in such a way as to include such an excretion range in the image capture range, captured imaging data includes excrement and the like as subjects. Of course, the above excretion range is preferably set in such a way that a user is not reflected, and the camera is preferably installed in such a way that a lens of the camera is also seen by the user. Furthermore, when the user uses the information processing system 1 in a hospital or a care facility, for example, the user is mainly a care receiver of a patient and the like.

The excretion information is information indicating the content of excretion, and in a simpler example, can be information indicating that excrement is feces (stool) or pee (urine). The excretion information may also include information indicating the color of excrement and other information such as the shape of a solid body when excrement is the solid body.

The acquisition unit 1a can acquire the excretion information by using, for example, a learned model, or by performing comparison based on image matching and the like. It is sufficient if the learned model is any model that outputs excretion information on the basis of the imaging data captured by the camera, and can be stored in a storage unit (not illustrated). For example, the learned model can be a model in which the above imaging data is input or data acquired by preprocessing the imaging data is input and excretion information (may be a plurality of types of information) is output. Note that it is sufficient if the learned model is generated by machine learning, regardless of an algorithm (machine learning algorithm), hyper parameters such as the number of layers, and the like. In this way, the acquisition unit 1a can acquire the excretion information by using the learned model on the basis of the imaging data.

On the other hand, in the configuration in which the acquisition unit 1a performs comparison such as image matching, it is sufficient if various image data to be compared or feature data thereof are associated with excretion information indicating the content of excretion and are stored in the storage unit (not illustrated). Then, the acquisition unit 1a may receive the imaging data from the camera and extract the features thereof. Thereafter, the acquisition unit 1a may perform comparison with the data stored in the storage unit and output excretion information indicated by data to be compared, which matches the data or has the highest matching rate.

Furthermore, the imaging data may include attached information such as imaging date and time and imaging conditions, and the learned model may also be a model in which not only the imaging data but also other information are input as parameters. The imaging conditions may include, for example, the resolution of a camera whose resolution can be set, and the zoom magnification of a camera having a zoom function.

Furthermore, the imaging data used for acquiring the excretion information may be, for example, data when an object is detected as a subject in the excretion range or a change such as a change in the color of stagnant water is detected. These detections can be performed, for example, by performing imaging with a camera at all times or at regular intervals and using imaging data acquired through the imaging. Alternatively, imaging may be performed on the basis of user detection results from separately provided user detection sensors (a load sensor provided on a toilet seat, other human detecting sensors, and the like), and imaging data at that time can be used for acquiring excretion information.

The generation unit 1b generates presentation information on the basis of the excretion information acquired by the acquisition unit 1a. In the simplest example, the presentation information may be the excretion information itself or information acquired by processing the excretion information for presentation. When the excretion information does not include date and time information indicating the acquisition date and time of the imaging data, the presentation information may be information including the excretion information and the date and time information. Of course, the presentation information may include other information.

Furthermore, as can be understood from the simplest example, the acquisition unit 1a and the generation unit 1b can also be configured to acquire the excretion information and the presentation information by using a learned model that outputs the excretion information and the presentation information on the basis of the imaging data captured by the camera. The learned model in this example may also be a model in which not only the imaging data but also other data are input. Furthermore, the learned model in this example can output the excretion information as the output of a certain intermediate layer and output the presentation information as the output of an output layer, for example. Note that the learned model in this example as well, it is sufficient if the learned model is generated by machine learning, regardless of an algorithm (machine learning algorithm), hyper parameters such as the number of layers, and the like.

The output unit 1c outputs the presentation information. The output unit 1c may also be used as, for example, a communication unit composed of a wired or wireless communication interface and the like. The output unit 1c may transmit the presentation information to an external alert apparatus (not illustrated) via the communication unit, for example, thus the alert apparatus can issue an alert on the basis of the presentation information. The output unit 1c may transmit the presentation information to an external server (not illustrated) via the communication unit, for example, thus the server can store the presentation information. The output unit 1c can also output print data (print job) for printing the presentation information to, for example, a printing apparatus built in an apparatus constituting the information processing system 1 or connected to the outside, via the communication unit. With this, the printing apparatus can print the presentation information.

The washing control unit 1d controls the washing function of the toilet bowl. Therefore, the washing control unit 1d is connected to or connectable to an apparatus having the washing function of the toilet bowl (for example, a hot water washing toilet seat such as a washlet (registered trademark) having a function of flushing the toilet), for example, via the communication unit. The washing target of the hot water washing toilet seat is user's buttocks and the like. The information processing system 1 may also include such a device or a toilet bowl integrated with hot water washing toilet seat.

In the aforementioned configuration, the present example embodiment is particularly characterized in a case where an object other than feces and urine (hereinafter, referred to as a foreign body) is included in the subject of the imaging data. This feature will be described. The foreign body may also be referred to as another object, may be liquid or solid as long as it is other than feces and urine, and may include, for example, any one or more of vomit, melena, blood vomiting (hematemesis), a urine absorbing pad, and a toilet paper core.

The acquisition unit 1a acquires information, which indicates whether a foreign body that is an object other than feces and urine is included in the imaging data captured by the camera as a subject excluding the toilet bowl and washing liquid for the toilet bowl, as at least a part of the excretion information. As described above, the excretion information may also include information indicating whether feces and urine are included.

When the acquisition unit 1a acquires information including the foreign body as the excretion information, the washing control unit 1d outputs a stop command for stopping the washing function to the toilet bowl side. Furthermore, when the acquisition unit 1a acquires the information including the foreign body as the excretion information, the generation unit 1b generates alert information as at least a part of the presentation information. The alert information may refer to information for presenting an alert, that is, information for issuing an alert sound or displaying an alert. With this, the output unit 1c can output the alert information. The output destination of the alert information may be, for example, a terminal apparatus, an alert apparatus, and the like that allow an observer such as a caregiver who cares for a user to be able to recognize the alert information.

The information processing system 1 may have the aforementioned storage unit and control unit (not illustrated), and the control unit may have the acquisition unit 1a, the generation unit 1b, the output unit 1c (or a part thereof), and the washing control unit 1d described above. The control unit can be implemented by, for example, a central processing unit (CPU), a working memory, a nonvolatile storage device that stores a program, and the like. The program may be a program for causing the CPU to perform the processes of the units 1a to 1d. Furthermore, the control unit provided in the information processing system 1 can also be implemented by, for example, an integrated circuit.

Furthermore, the information processing system 1 according to the present example embodiment can also be configured as a single information processing apparatus, or can also be configured as a plurality of apparatuses with distributed functions. In the latter case, it is sufficient if each apparatus is provided with the control unit, the communication unit, and the storage unit, and the like as necessary, and the plurality of apparatuses are connected to one another as necessary by wired or wireless communication and implement functions as the information processing system 1 in cooperation with one another.

Moreover, the information processing system 1 may also include the aforementioned camera, and when the information processing system 1 is configured as a single information processing apparatus, the information processing apparatus includes the camera. In this way, when the information processing system 1 is configured as a single information processing apparatus, the information processing apparatus includes the aforementioned camera and is preferably installed on a toilet bowl of a toilet in such a way that the camera is disposed in such a way as to include in an image capture range an excretion range of excrement in the toilet bowl. In such a case, the information processing apparatus may also be referred to as an excretion information acquisition apparatus.

As described above, in the present example embodiment, when a foreign body other than excrement is detected, alert information is output (notified) to a caregiver and the like, and a washing function of washing a toilet bowl of a toilet is stopped to prevent the foreign body from being flushed. Thus, in the present example embodiment, even when a user uses the washing function, since the washing function is stopped, the foreign body can be left without being flushed and then can be inspected as a sample and the like. Furthermore, since the foreign body is not flushed and alert information indicating the detection of the foreign body is output, a user's observer and the like can rush to the toilet, which can prevent a user from feeling the confusion caused by not flushing the foreign body.

Furthermore, the output destination of the alert information is not limited to one place, and may be set to simultaneously include from, for example, a terminal apparatus or an alert apparatus outside the toilet to an alert apparatus provided in any of the toilet. In such a case, by outputting a voice such as "Washing function is stopped because foreign body was detected" in the toilet, it is possible to prevent the aforementioned confusion.

In this way, according to the present example embodiment, it is possible to collect excretion information indicating the content of excrement in a toilet bowl without having to ask a user of a toilet and prevent flushing of a foreign body, other than the excrement, when present in the toilet bowl.

Second Example Embodiment

Figure 2:
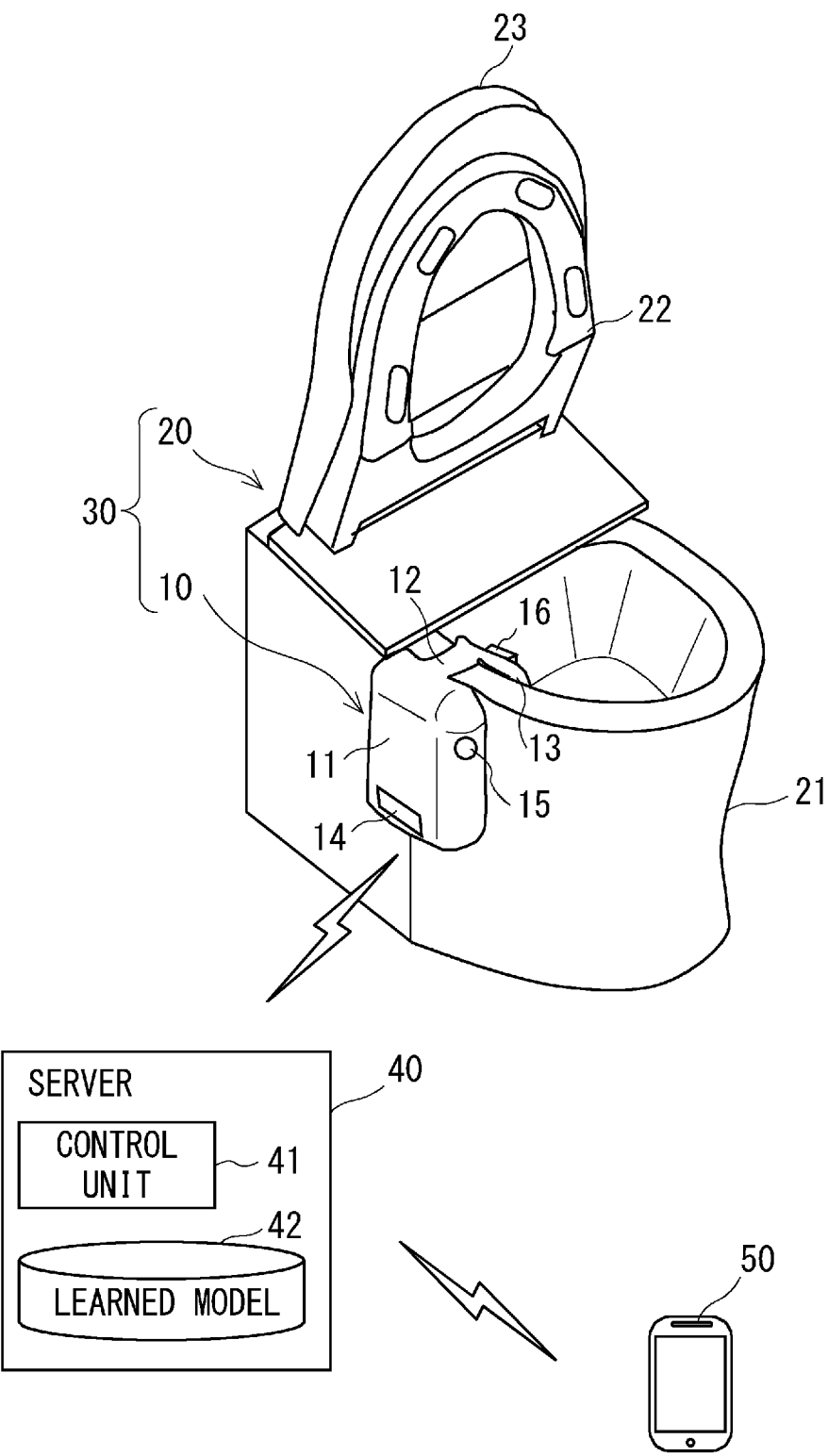
FIG. 2 is a diagram illustrating a configuration example of an information processing system according to a second example embodiment.
Figure 3:
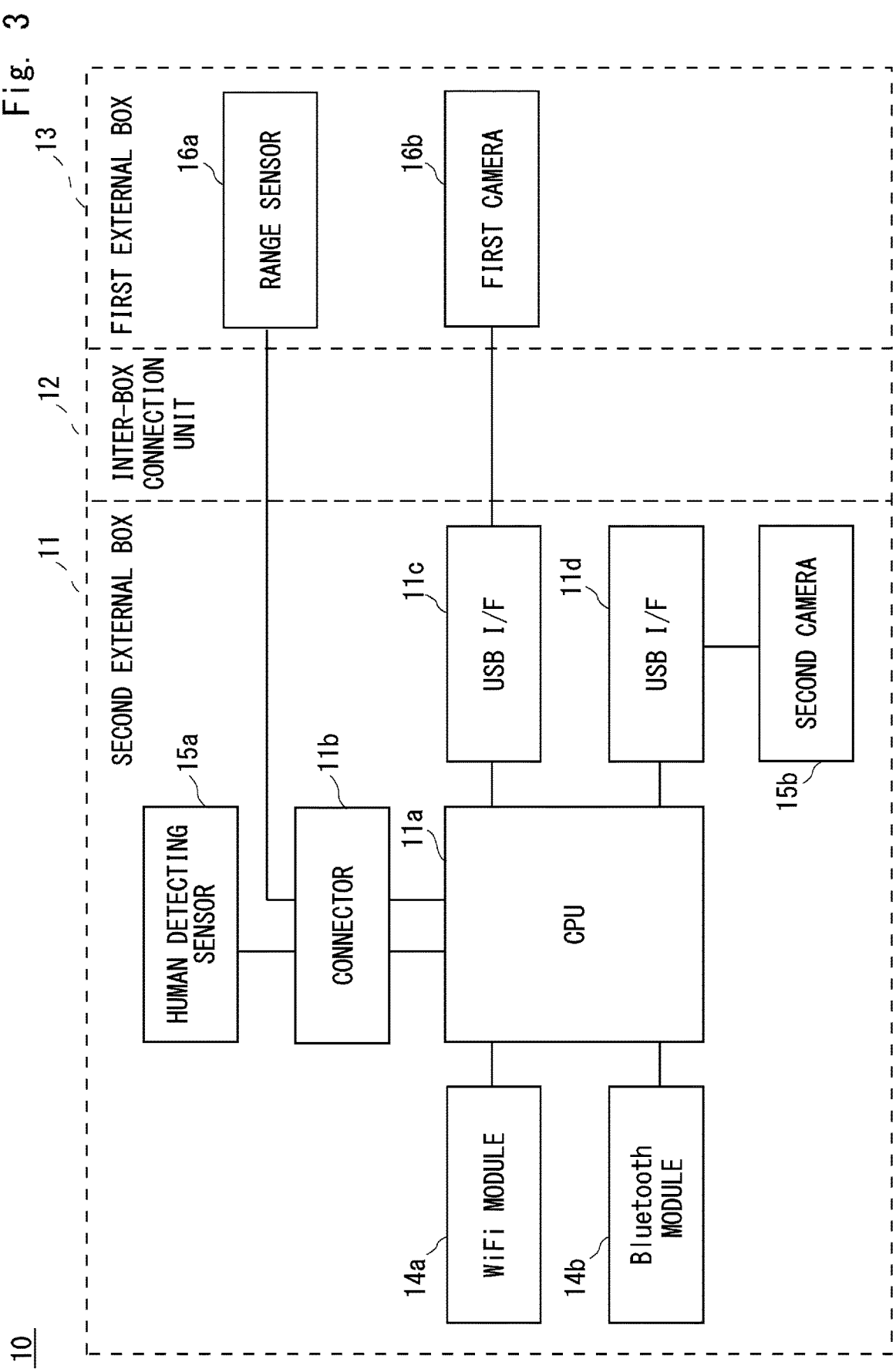
FIG. 3 is a block diagram illustrating a configuration example of an information processing apparatus in the information processing system in FIG. 2.
Figure 4:
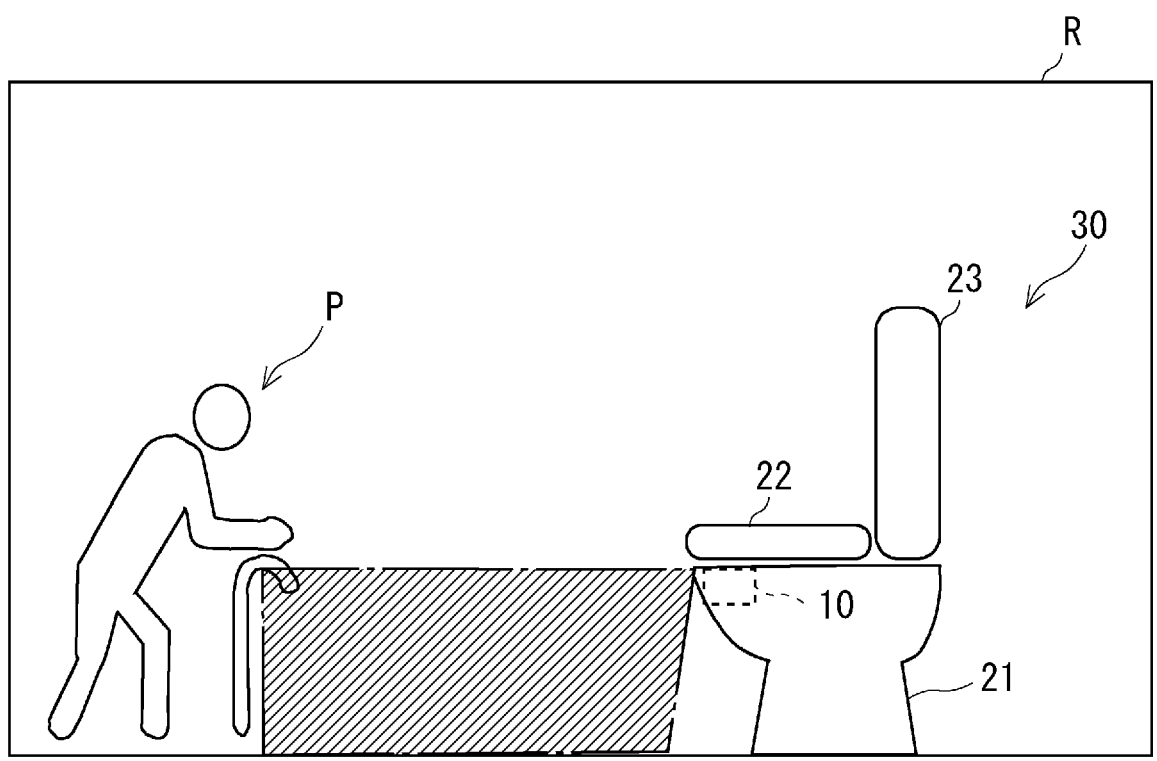
FIG. 4 is a conceptual diagram illustrating an example of a user detection range by the information processing apparatus in the information processing system in FIG. 2.

A second example embodiment will be described with reference to FIG. 2 to FIG. 19 while focusing on differences with the first example embodiment, but various examples described in the first example embodiment can be applied. FIG. 2 is a diagram illustrating a configuration example of an information processing system according to the second example embodiment, and FIG. 3 is a block diagram illustrating a configuration example of an information processing apparatus in the information processing system in FIG. 2. Furthermore, FIG. 4 is a conceptual diagram illustrating an example of a user detection range by the information processing apparatus in the information processing system in FIG. 2.

The information processing system according to the present example embodiment (hereinafter, the present system) may be a system in which a part thereof is installed in a toilet to record and present excretion information and predict excretion, and will be described below in detail.

The present system may include an information processing apparatus 10 attached to a toilet bowl 20, a server 40 wirelessly connected to the information processing apparatus 10, and a terminal apparatus 50 wirelessly connected to the server 40. Note that these components may be connected to one another within, for example, one wireless local area network (LAN). Furthermore, although the information processing apparatus 10 will be described below as being installed on the toilet bowl 20 of the toilet, it is sufficient if at least a part of the information processing apparatus 10, such as a camera for capturing imaging data, is installed on the toilet bowl 20. The toilet bowl 20 may be provided on the body 21 thereof with, for example, a toilet seat 22 having a hot water washing function for user washing and a toilet seat cover 23 for closing the toilet seat 22.

The information processing apparatus 10 may be a toilet-installation type (toilet bowl-installation type in this example) apparatus, and records excrement, presents (notifies and the like) excretion information, and predicts excretion in cooperation with the server 40 and the terminal apparatus 50. The information processing apparatus 10 and the toilet bowl 20 can form, for example, a toilet bowl 30 with a function of outputting excretion information. This function is mainly performed by the information processing apparatus 10 in cooperation with the server 40 and the like, and will be described below.

Furthermore, the shape of the information processing apparatus 10 is not limited to the shape illustrated in FIG. 2, and may be configured such that all or some of the functions of the information processing apparatus 10 are embedded in the toilet seat 22 and the like, for example. Furthermore, some of the functions of the information processing apparatus 10 may also be provided on the toilet seat 22 side. For example, when the information processing apparatus 10 is not provided with a range sensor 16a to be described below and the toilet seat 22 is provided with a weight sensor, it is also possible to adopt a configuration in which the information processing apparatus 10 receives information from the weight sensor by wireless or wired communication. Similarly, when the information processing apparatus 10 is not provided with a first camera 16b to be described below and the toilet seat 22 side is provided with a camera, it is also possible to adopt a configuration in which the information processing apparatus 10 receives imaging data from the camera by wireless or wired communication.

The server 40 may include a control unit 41 and a storage unit 42 that stores a learned model. The control unit 41 can be implemented by, for example, a CPU, a working memory, a nonvolatile storage device that stores a program, and the like. Furthermore, the control unit 41 can also be implemented by, for example, an integrated circuit. The storage device can be used as the storage unit 42, and the program may be a program for causing the CPU to implement the function of the server 40.

The terminal apparatus 50 is a terminal apparatus owned by an observer of a user of the toilet and may be a portable information processing apparatus, but it may be an installation type apparatus. In the former case, the terminal apparatus 50 may be a mobile phone (also including a smartphone), a tablet, a mobile PC, and the like. Although not illustrated, the terminal apparatus 50 may also include a control unit that controls the entire terminal apparatus 50, and a storage unit. Similarly to the control unit 41, the control unit can be implemented by, for example, a CPU, a working memory, a storage device, and the like. Furthermore, a program stored in the storage device may be a program for causing the CPU to implement the function of the terminal apparatus 50.

Next, a detailed example of the information processing apparatus 10 will be described. The information processing apparatus 10 can be composed of, for example, two apparatuses as illustrated in FIG. 2 and FIG. 3. More specifically, the information processing apparatus 10 may include, as its housing, two boxes, for example, a first external box 13 and a second external box 11. Furthermore, the information processing apparatus 10 may include an inter-box connection unit (inter-box connection structure) 12 that connects the first external box 13 and the second external box 11. In this example, the information processing apparatus 10 may be installed on the body 21 of the toilet bowl 20 as follows, for example. That is, the information processing apparatus 10 may be installed on the toilet bowl 20 by placing the inter-box connection unit 12 on the edge of the body 21 in such a way that the first external box 13 is arranged on the inside of the body 21 (side where an excretion range of excrement is located) and the second external box 11 is arranged on the outside of the body 21.

The first external box 13 may accommodate, for example, the range sensor 16a and the first camera 16b. The second external box 11 may accommodate, for example, a CPU 11a, a connector 11b, USB I/Fs 11c and 11d, a WiFi module 14a, a Bluetooth module 14b, a human detecting sensor 15a, and a second camera 15b. Note that USB is an abbreviation for universal serial bus, and USB, WiFi, and Bluetooth are all registered trademarks (the same applies below).

Note that the second external box 11 is not provided with various I/Fs or connectors and may also be directly connected to the CPU 11a. Furthermore, the information processing apparatus 10 is not provided with the CPU 11a, and may simply include sensors and cameras for acquiring various data and have only function of transmitting various data to the server 40 side.

As illustrated in FIG. 3, the first external box 13 and the second external box 11 are connected by the connector 11b and an interface exemplified by the USB I/F 11c, and the connection line is provided inside the inter-box connection unit 12, which configures one information processing apparatus 10.

The first external box 13 will be described.

The range sensor 16a is a sensor that measures a distance to an object (buttocks of a user of the toilet bowl 20) and detects that the user is sitting on the toilet seat 22, and detects that the object is sitting on the toilet seat 22 when a certain time elapses beyond a threshold. Furthermore, when there is a change in the distance to the object after sitting, the range sensor 16a detects that the user has left the toilet seat 22.

As the range sensor 16a, for example, an infrared sensor, a ultrasonic sensor, an optical sensor, and the like can be adopted. When an optical sensor is adopted as the range sensor 16a, it is sufficient that a transmission/reception element is disposed in such a way that light (not limited to visible light) can be transmitted/received from a hole provided in the first external box 13. In the transmission/reception element, a transmission element and a reception element may be configured separately or may be integrated. The range sensor 16a is connected to the CPU 11a via the connector 11b and may transmit a detection result to the CPU 11a side.

The first camera 16b is an example of a camera that captures the imaging data that is a source of the acquisition of the excretion information by the acquisition unit 1a in FIG. 1, and may be an optical camera whose lens portion is disposed in the hole provided in the first external box 13. As described in the first example embodiment, the first camera 16b is installed to include in an image capture range the excretion range of excrement in the toilet bowl 20 of the toilet. The first camera 16b is connected to the CPU 11a via the USB I/F 11c and transmits the imaging data to the CPU 11a side.

The second external box 11 will be described.

The CPU 11a is an example of a main control unit of the information processing apparatus 10, and controls the entire information processing apparatus 10. The connector 11b connects the human detecting sensor 15a and the CPU 11a and connects the range sensor 16a and the CPU 11a. The USB I/F 11c connects the first camera 16b and the CPU 11a, and the USB I/F 11d connects the second camera 15b and the CPU 11a.

The human detecting sensor 15a is a sensor that detects the presence of a person (entry and exit of a person) in a specific area (measurement area range of the human detecting sensor 15a) as indicated by a hatched area in FIG. 4, for example. The hatched area in FIG. 4 is a part of a toilet room R. As the human detecting sensor 15a, for example, an infrared sensor, a ultrasonic sensor, an optical sensor, and the like can be adopted regardless of the detection method. The human detecting sensor 15a is connected to the CPU 11a via the connector 11b, and when a person is detected in the specific area, the human detecting sensor 15a transmits a detection result to the CPU 11a. The detection result can be transmitted to the server 40 by the CPU 11a via the WiFi module 14a.

The second camera 15b may be an optical camera whose lens portion is disposed in a hole provided in the second external box 11, and is an example of a camera that acquires face image data by taking a face image of a user of the toilet in order to identify the user. The second camera 15b may be installed on the toilet bowl 20 to include a user's face in an image capture range, but may also be installed in the toilet room where the toilet bowl 20 is installed.

The Bluetooth module 14*b* is an example of a receiver that receives identification data for identifying a user from a Bluetooth tag held by the user, and may also be replaced with a module on the basis of another near-field communication standard. The Bluetooth tag held by the user may be set as a different ID for each user, and may be held by the user by being embedded in a wristband and the like, for example.

The WiFi module 14*a* is an example of a communication apparatus that transmits various acquired data to the server 40, and may also be replaced with a module adopting another communication standard. The face image data acquired by the second camera 15*b* and the identification data acquired by the Bluetooth module 14*b* may be transmitted to the server 40 by the CPU 11*a* via the WiFi module 14*a*.

The CPU 11*a*, the USB I/F 11*c*, the WiFi module 14*a*, and the server 40 may be examples of the acquisition unit 1*a* in FIG. 1, and acquire excretion information on the basis of the imaging data captured by the first camera 16*b*. In such a case, the server 40 may be responsible for the main process of acquiring the excretion information from the imaging data. The server 40 in the example of FIG. 2 inputs the imaging data into the learned model and acquires the excretion information. Furthermore, the server 40 mainly acquires information, which indicates whether a foreign body that is an object other than feces and urine is included in the imaging data as a subject excluding the toilet bowl and washing liquid for the toilet bowl, as at least a part of the excretion information.

The CPU 11*a*, the WiFi module 14*a*, and the server 40 may be examples of the generation unit 1*b* in FIG. 1. In such a case, the server 40 may be responsible for the main process of generating presentation information from the excretion information. The server 40 in the example of FIG. 2 inputs the imaging data into the learned model and acquires the presentation information together with the excretion information. Furthermore, when information including a foreign body has been acquired as the excretion information (same meaning even when it is acquired), the server 40 mainly generates alert information as at least a part of the presentation information.

Although the description is based on the example in which the learned model outputs both the excretion information and the presentation information, the excretion information and the presentation information may also be acquired by two separate learned models as described in the first example embodiment. In such a case, a case where information including the above foreign body has been acquired is synonymous with a case where the imaging data is input imaging data for acquiring the information including the above foreign body.

The CPU 11*a*, the WiFi module 14*a*, the server 40, and the terminal apparatus 50 may be examples of the output unit 1*c* in FIG. 1. In such a case, the terminal apparatus 50 may be responsible for the main process of outputting alert information at the time of occurrence of a foreign body as the presentation information, and the terminal apparatus 50 receives the presentation information generated by the server 40, and displays the presentation information and/or outputs the presentation information by voice.

Furthermore, the server 40 may store the presentation information other than the alert information in the storage unit 42 and the like, and output the presentation information in response to access from, for example, the terminal apparatus 50. Particularly, it is desirable to adopt such an output example for an excretion diary and the like to be described below, thus a user can browse the excretion diary from the terminal apparatus 50 when the user desires.

The CPU 11*a* and an interface (not illustrated) between the toilet seat 22 and the CPU 11*a* may be examples of the washing control unit 1*d* in FIG. 1. As for the washing function, it is sufficient if the amount of water flowing into the toilet bowl 20 is controlled using the existing technology (the toilet seat 22 is controlled in this example). Then, the CPU 11*a* receives the excretion information from the server 40 via the WiFi module 14*a*, and outputs a stop command for stopping the washing function to the toilet bowl side (the toilet seat 22 in this example) when the information including the foreign body is acquired as the excretion information, thus the washing function is stopped.

For example, by notifying a remote-controllable power supply tap connected to a power cord of the toilet seat 22 of the toilet of power interruption, the washing function of the toilet bowl 20 of the toilet is stopped. More specifically, it is possible to supply power to the toilet seat 22 via the Internet of things (IoT) tap, output a stop command to the IoT tap, and turn off the power. In such a case, the stop command may be transmitted by, for example, the CPU 11*a* via the Bluetooth module 14*b*.

In this way, in the present system, by inputting imaging data acquired by capturing the image capture range by the first camera 16*b* into the learned model (or by comparing the imaging data with other data), it is possible to check whether it is excrement or non-excrement. Furthermore, in the case of the excrement, the shape, color, and amount of the excrement may be ascertained, and particularly, this ascertainment becomes more accurate by using a learned model learned preferably. Furthermore, in the present system, when it is determined that an object to be imaged is not excrement, alert information (alarm) is notified to an observer such as a caregiver, and the washing function of the toilet bowl 20 is stopped.

The server 40 receives the face image data acquired by the second camera 15*b* via the WiFi module 14*a*, and performs a facial recognition process by comparing the face image data with recognition data stored in advance, for example, feature points thereof and the like, thereby acquiring identification data associated with the matched recognition data. In this way, the server 40 may acquire the identification data (identification data for identifying a user), that is, specify a user.

Furthermore, since the server 40 may acquire the face image data of a user of the toilet bowl 20 at the time of acquisition of the imaging data together with the imaging data from the information processing apparatus 10, the server 40 may identify a user on the basis of the face image data and generate presentation information for each user. By the facial recognition process, the server 40 may specify the closest user as a current toilet user. In this way, the aforementioned identification data may be used as data identifying a user by performing the facial recognition process on the basis of the face image data captured by the second camera 15*b* in the toilet bowl 20 or a room where the toilet bowl 20 is installed (private room of the toilet). It is preferable not to store the face image data captured by the second camera 15*b*, in consideration of privacy.

Furthermore, the terminal apparatus 50 may output the presentation information to each user. Furthermore, when one or a plurality of presentation target persons (for example, an observer in charge when a user is a care receiver) are determined in advance for each user, the server 40 may output presentation information to terminal apparatuses 50 used by the presentation target persons. An example of the observer includes a caregiver, also includes a doctor according to occasions, but may also include a helper other than a caregiver. Furthermore, the observer may be other persons depending on the application environment of the present system.

Moreover, the server 40 receives the identification data (personal recognition data) acquired by the Bluetooth module 14b via the WiFi module 14a, and performs user recognition by comparing the identification data with recognition identification data stored in advance. For example, when a caregiver holding his/her Bluetooth tag and a care receiver holding his/her Bluetooth tag enter a toilet together, the care receiver may be selected as a user. In this way, the server 40 may acquire the identification data (identification data for identifying a user), that is, specify a user.

Furthermore, since the server 40 may acquire the identification data of the user of the toilet bowl 20 at the time of acquisition of the imaging data together with the imaging data from the information processing apparatus 10, the server 40 may generate presentation information for each user on the basis of the identification data. Then, the terminal apparatus 50 may output the presentation information to each user. Furthermore, when one or a plurality of presentation target persons are determined in advance for each user, the server 40 may output presentation information to terminal apparatuses 50 used by the presentation target persons.

In such an example, it can be said that a user is specified from two types of data, that is, the face image data and the identification data, and two specific functions are provided, but of course, a user may be specified by either one. For example, the present system has both specific functions, and may select one of them at the time of operation. Alternatively, the present system may have only one of the specific functions.

Furthermore, when the presentation information is alert information at the time of occurrence of a foreign body, the following process may also be performed. When the server 40 outputs alert information to terminal apparatuses 50 of a plurality of caregivers and then receives a notification from the terminal apparatus 50 of a certain caregiver to assist a care receiver, subsequent alert information may be output to only the terminal apparatus 50 of the caregiver who has declared such assistance. The subsequent alert information may be output until exit is detected after entry is detected, as will be described below.

As described above, the detection result of the human detecting sensor 15a may be transmitted to the server 40. Since the detection result may be used for determining entry/exit to/from the toilet, even when there is no detection, the server 40 can acquire the information. When the detection result is received from the information processing apparatus 10, the server 40 stores data (entry/exit data), which indicates entry/exit to/from the toilet where the toilet bowl 20 is installed, in the storage unit 42 and the like in association with the identification data of the user specified as described above. Note that the entry/exit data may also include the identification data.

Then, the server 40 generates presentation information for each user on the basis of the identification data and the entry/exit data. With this, the server 40 may output the presentation information to each user, and even when there are a plurality of defecations, the server 40 may handle the defecations as excretion information and presentation information for a series of defecation processes by using the entry/exit data.

Furthermore, in the present system, when the human detecting sensor 15a detects a person, the second camera 15b may take a picture of the target person who has entered the toilet. With this, face recognition may be performed only when a person is detected.

Furthermore, the server 40 may ascertain a case of entering or exiting the toilet independently by using the data acquired by the human detecting sensor 15a and the identification data identifying a user, and notify the terminal apparatus 50 of presentation information including only such entry/exit. In such a case, when one or a plurality of presentation target persons (for example, an observer such as a caregiver in charge when a user is a care receiver) are determined in advance for each user, the server 40 may transmit a notification to terminal apparatuses 50 used by the presentation target persons.

Furthermore, the same concept may be applied to processing based on the data detected by the range sensor 16a. That is, the server 40 may refer to the data acquired by the range sensor 16a, check that the distance is short for a certain period of time or more or that the distance exceeds the set threshold, and detect a state of sitting on the toilet seat for a long time or a state of leaving the toilet seat 22. Then, the server 40 may notify terminal apparatuses 50 used by one or a plurality of notification target persons of presentation information indicating the state of sitting on the toilet seat for a long time or the state of leaving the toilet seat 22.

Furthermore, when the server 40 receives a notification from a terminal apparatus 50 of a certain caregiver to assist a care receiver after transmitting the presentation information to the terminal apparatuses 50 of the plurality of caregivers, the server 40 may transmit a notification to only the terminal apparatus 50 of the caregiver who has declared such assistance. The subsequent notification may be transmitted until exit is detected.

Furthermore, the server 40 may calculate an excretion timing on the basis of the excretion information and the date and time of an excretion behavior, and generate information for notifying the excretion timing as at least a part of the presentation information. The date and time of the excretion behavior may be acquired by any one of the date and time of imaging the imaging data, the date and time of identifying a subject, the date and time of entering and exiting, the date and time of sitting, the date and time of leaving, the intermediate date and time from sitting to leaving, and the like.

The notification destination of the presentation information in such a case may also be, for example, one or a plurality of observers determined in advance. Furthermore, the calculation process may be a process of predicting the excretion timing, whereby when the excretion timing approaches (predetermined time before the excretion timing), scheduled excretion may be promoted.

The excretion timing may be calculated as a constant period of defecation desire through the day or a constant period from an initial time (time of waking up or time of first defecation in the day). In such a case, in a simpler example, the excretion timing may be an average interval time or an average interval time from the initial time. However, as the excretion timing, a timing of promoting the defecation desire of a user may also be acquired according to the time period by means of the learned model, and the like. Furthermore, it is preferable that the excretion timing is calculated and notified separately for urination and defecation on the basis of the excretion information. Furthermore, the excretion timing is also notified to a terminal apparatus held by a care receiver, which makes it possible to reduce incontinence and the like of the care receiver and support the independence thereof.

Next, examples of notifying presentation information to the terminal apparatus 50 will be described with reference to FIG. 5 to FIG. 9. FIG. 5 to FIG. 9 are diagrams for explaining examples of a notification in a terminal apparatus in the information processing system in FIG. 2. Note that the presentation information to be described below is presented in a timely manner and particularly not described, may be updated as soon as it is acquired.

Figure 5:
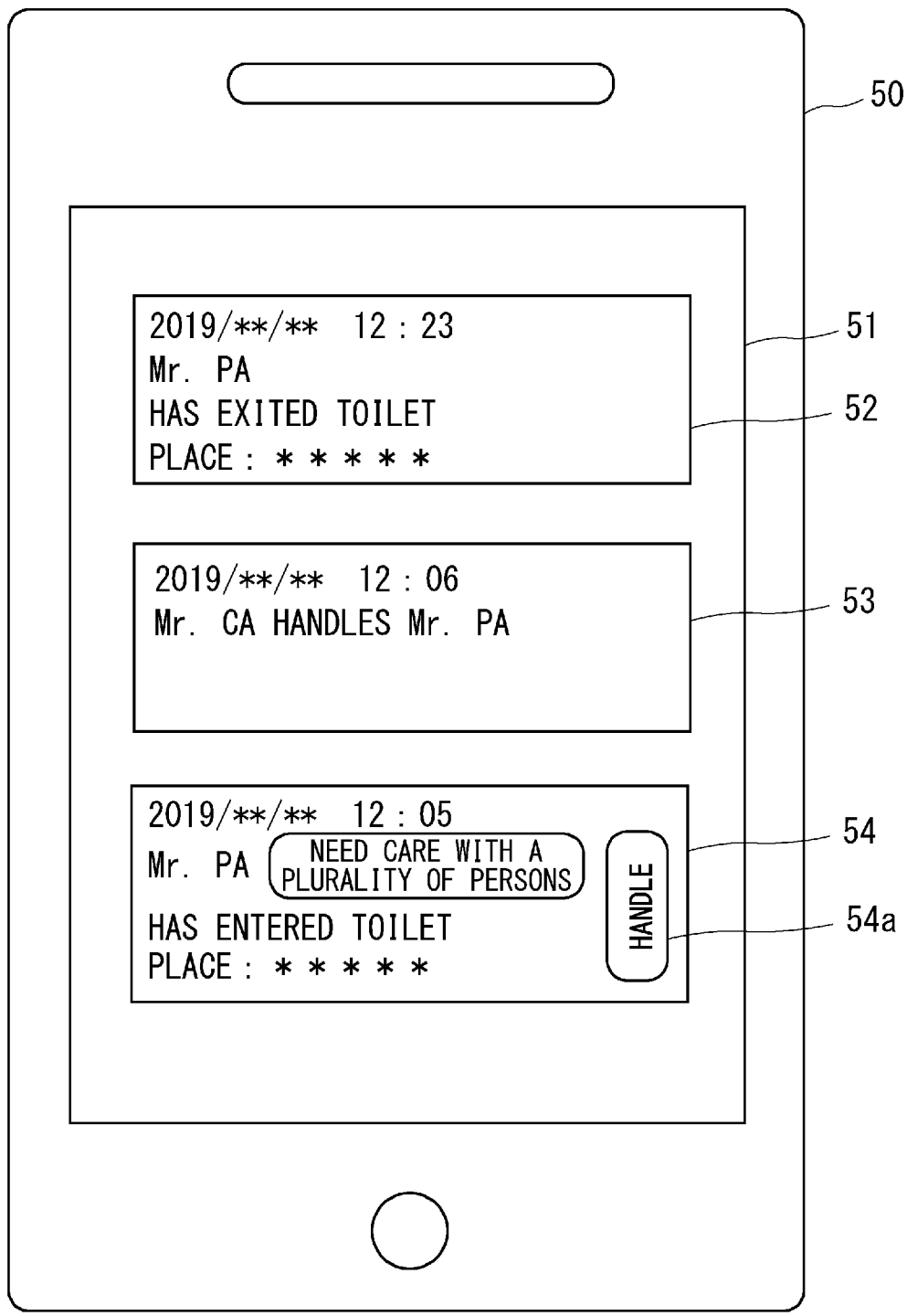
FIG. 5 is a diagram for explaining an example of a notification in a terminal apparatus in the information processing system in FIG. 2.

As illustrated in FIG. 5, the terminal apparatus 50 may notify presentation information 52 to 54 in a timely manner on the display screen 51 thereof. The presentation information 54 is an example of information for identifying a user (Mr. PA in this example) when the human detecting sensor 15a detects a person and notifies that the user enters the toilet. The user identification may be acquired as a result of performing the facial recognition process based on the face image data acquired by the second camera 15b or the identification process received by the Bluetooth module 14b when the human detecting sensor 15a detects the person. In a face recognition person list or an identification person list, care receivers who need care with a plurality of persons are recorded, and when the user is a care receiver, the presentation information 54 may include information, which notifies that the user is a target person who need care with a plurality of persons, next to the name (Mr. PA in this example). Furthermore, the presentation information 54 may include a button 54a for selecting to notify that the user handles the care receiver.

The present system may be configured to display the presentation information 53 on the terminal apparatus 50 of another caregiver (and the terminal apparatus 50 of a caregiver CA) when the caregiver CA selects the button 54a on the terminal apparatus 50. The presentation information 53 may include information indicating that Mr. CA handles to Mr. PA. Particularly, the present system may also be configured to notify a terminal apparatus 50 used by another caregiver of handling of the care receiver when the button 54a is selected in the case of a target person who need care with a plurality of persons as in the case of Mr. PA. Furthermore, the presentation information 52 is an example of information for notifying the exit from the toilet when the detection state is changed to a non-detection state for Mr. PA.

Figure 6:
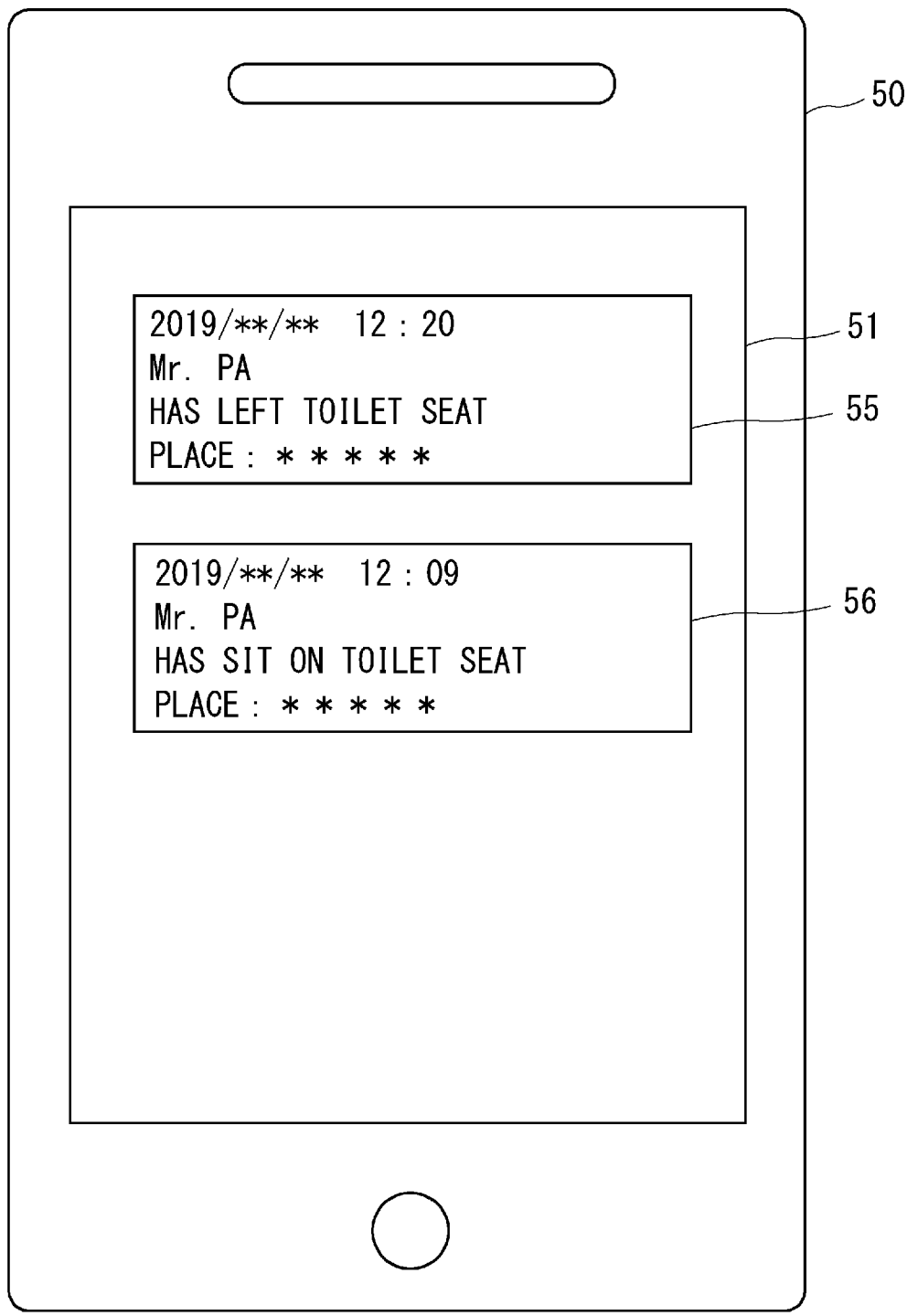
FIG. 6 is a diagram for explaining an example of a notification in a terminal apparatus in the information processing system in FIG. 2.

As illustrated in FIG. 6, the terminal apparatus 50 may notify presentation information 55 and 56 in a timely manner on the display screen 51 thereof. The presentation information 56 is an example of information for identifying a user (Mr. PA in this example) when the range sensor 16a detects sitting on the toilet seat 22 and notifying that the user (Mr. PA in this example) sits on the toilet seat 22. The user identification is not necessary, for example, after the presentation information 54 is presented because it has already been processed, and may be performed as follows when the presentation information 54 is not presented. That is, the user identification may be acquired as a result of performing the facial recognition process based on the face image data acquired by the second camera 15b or the identification process received by the Bluetooth module 14b when the range sensor 16a detects the sitting. Furthermore, the presentation information 55 is an example of information for notifying that Mr. PA has left the toilet seat 22 when the detection state is changed to a non-detection state for Mr. PA.

Figure 7:
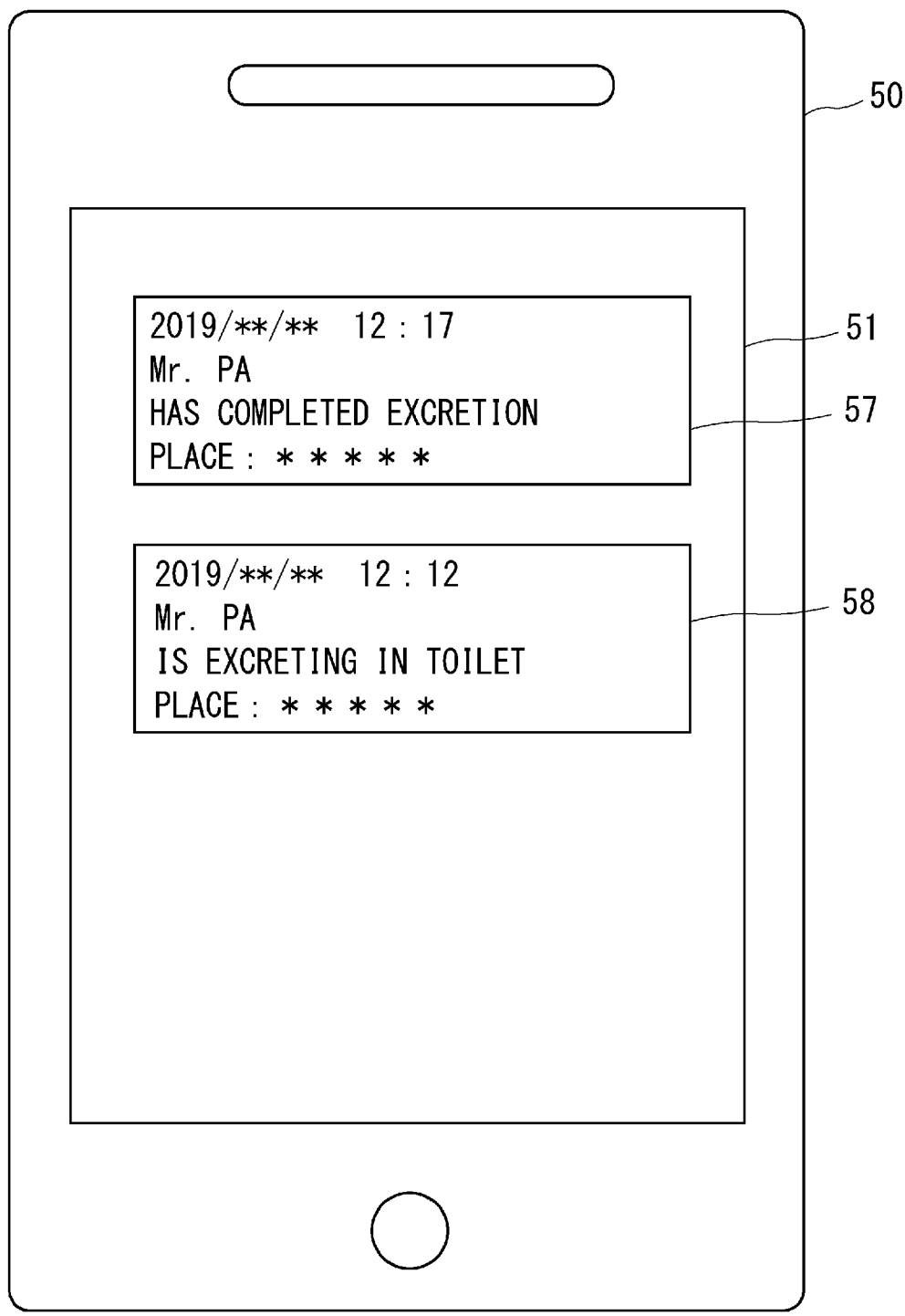
FIG. 7 is a diagram for explaining an example of a notification in a terminal apparatus in the information processing system in FIG. 2.

As illustrated in FIG. 7, the terminal apparatus 50 may notify presentation information 57 and 58 in a timely manner on the display screen 51 thereof. The presentation information 58 is an example of information for identifying a subject from the imaging data acquired by the first camera 16b, identifying a user (Mr. PA in this example) when the subject is excrement, and notifying that the user is excreting. The user identification is not necessary, for example, after the presentation information 54 and 56 are presented because it has already been processed, and may be performed as follows when the presentation information 54 and 56 are not presented. That is, the user identification may be acquired as a result of performing the facial recognition process based on the face image data acquired by the second camera 15b or the identification process received by the Bluetooth module 14b when the subject is identified from the face image data acquired by the first camera 16b.

Furthermore, the presentation information 57 is an example of information for notifying the completion of excretion of Mr. PA when a certain period of time has elapsed from the end of identification of excrement. Furthermore, the present system can also be configured to newly acquire imaging information from the first camera 16b instead of determining whether a certain period of time has elapsed, and to notify the completion of excretion when and there is no excrement or another foreign body.

Figure 8:
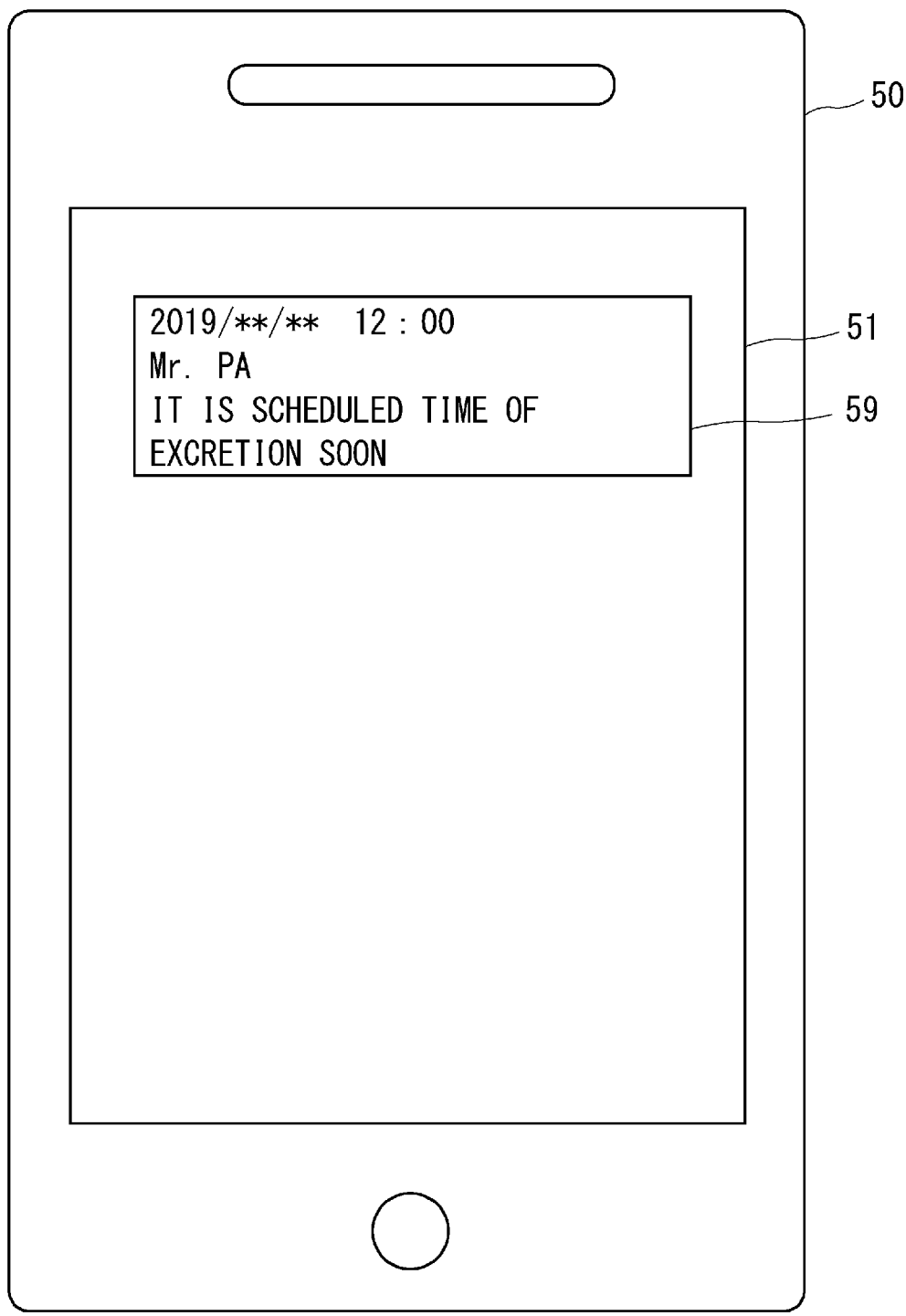
FIG. 8 is a diagram for explaining an example of a notification in a terminal apparatus in the information processing system in FIG. 2.

As illustrated in FIG. 8, the terminal apparatus 50 may notify presentation information 59 in a timely manner on the display screen 51 thereof. As described above, the server 40 may be configured to receive the date and time of imaging the imaging data (or the date and time when the excrement is identified) acquired by the first camera 16b from the information processing apparatus 10, and to record the received date and time. Then, as described above, the server 40 may calculate the scheduled data and time (excretion timing) of an excretion behavior for each user, and record the calculated date and time. The presentation information 59 is an example of information for notifying that the scheduled data and time of a user (Mr. PA in this example) approaches, on the basis of the excretion timing for each user calculated in this way. Furthermore, the present system may also register a terminal apparatus used by the user (Mr. PA in this example) in the server 40, and in such a case, it is also preferable to notify the terminal apparatus of a notification for informing the excretion schedule as illustrated in the presentation information 59.

Figure 9:
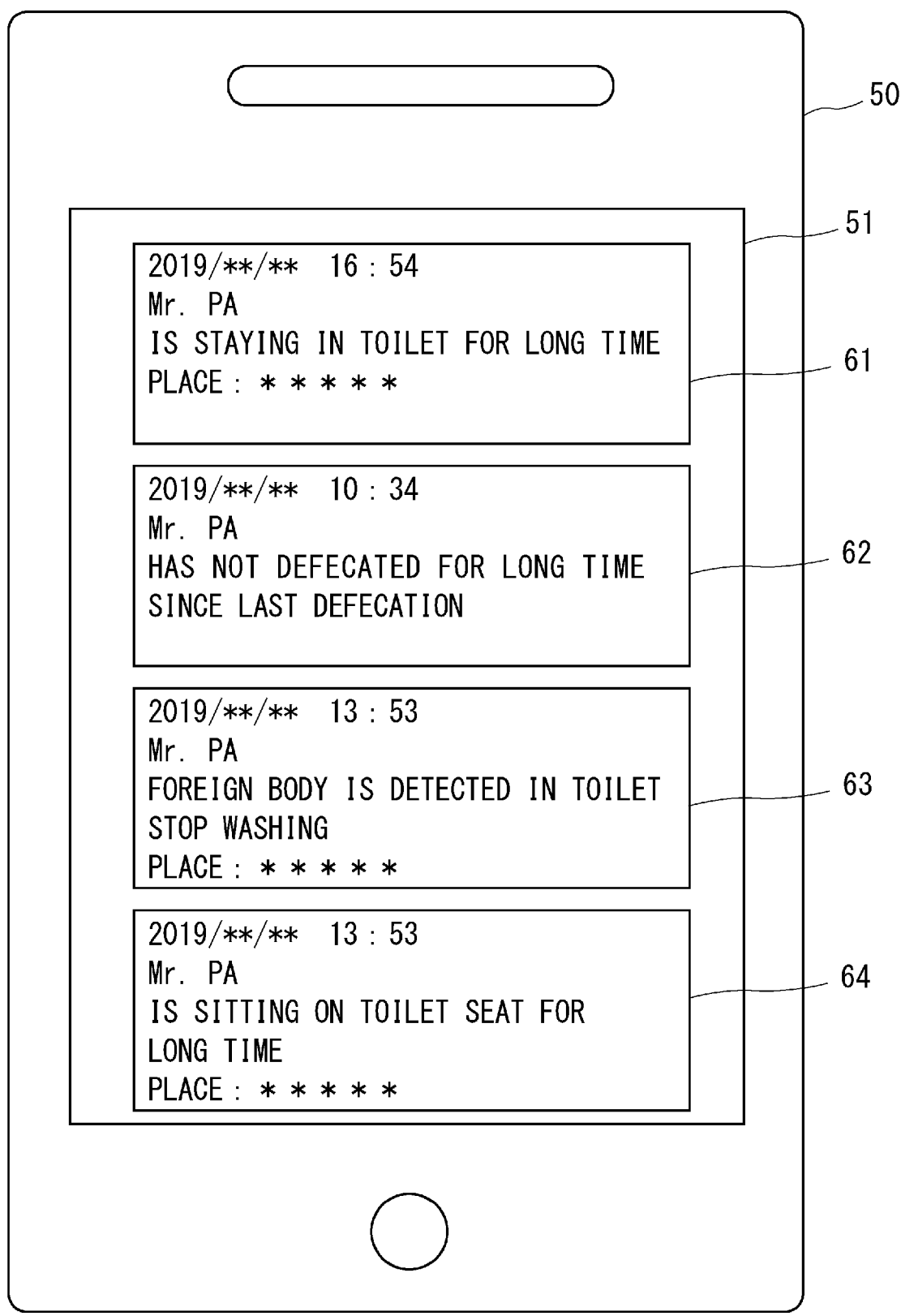
FIG. 9 is a diagram for explaining an example of a notification in a terminal apparatus in the information processing system in FIG. 2.

As illustrated in FIG. 9, the terminal apparatus 50 may notify presentation information 61 to 64 in a timely manner on the display screen 51 thereof. The presentation information 64 is an example of information for identifying a user when the detection of the range sensor 16a or the human detecting sensor 15a has elapsed for a certain period of time, and notifying that the user is sitting on the toilet seat of the toilet for a long time because it is assumed that some abnormality has occurred in the user. It can be said that this information is also a kind of alert information. The user identification is not necessary, for example, after the presentation information 54, 56, and 57 are presented because it has already been processed, and may be performed as follows when the presentation information 54, 56, and 57 are not presented. That is, the user identification may be acquired as a result of performing the facial recognition process based on the face image data acquired by the second camera 15b or the identification process received by the Bluetooth module 14b when the detection of the range sensor 16a or the human detecting sensor 15a has elapsed for a certain period of time.

Furthermore, the presentation information 63 is an example of alert information for identifying a subject from the imaging data acquired by the first camera 16b, identifying a user (Mr. PA in this example) when the subject is a foreign body other than excrement, and notifying that the foreign body has been mixed (detected) with respect to the user. The user identification is the same and is not necessary when it has already been processed. When it has not been processed, if the subject is identified from the imaging data acquired by the first camera 16b, the user identification may be acquired as a result of performing the facial recognition process or the identification process. Furthermore, simultaneously with the output of the presentation information 63, the information processing apparatus 10 notifies the remote-controllable power supply tap connected to the power cord of the toilet of power interruption, and stops the washing function of the toilet.

Furthermore, in the present system, the date and time when excrement is identified from the imaging data acquired by the first camera 16b may be recorded in the server 40. The presentation information 62 is an example of information for notifying that a care receiver has not defecated for a long time because it is assumed that constipation has occurred in the care receiver when there is no defecation record for a certain period of time since the last defecation. Furthermore, the presentation information 61 is an example of information for notifying that the care receiver is staying in the toilet for a long time when there is a reaction of the range sensor 16a for a certain period of time even though excretion and urination have been completed. It can be said that the presentation information 62 and 61 are also a kind of alert information.

Furthermore, in the present system, preferably, the processing content (for example, a notification of alert information) of the aforementioned presentation process is configured to be set by a user (for example, an observer) from the terminal apparatus 50, for example. Therefore, for example, the server 40 may be configured to store setting content for each observer and perform processing accordingly. With this, for each observer, it is possible to enable/disable the display or non-display of various alarms or notifications. In a more detailed example, in the present system, preferably, it is also possible to make settings such as "a certain observer CA receives alert information of a certain care receiver PA, but does not receive other information".

In the above, the present system has been described on the premise that there is only one toilet bowl 20 (only one toilet room). However, in the present system, it is preferable to collect imaging data for a plurality of toilets and acquire excretion information. With this, the present system may also be applied even when a user may use two or more toilets.

Figure 10:
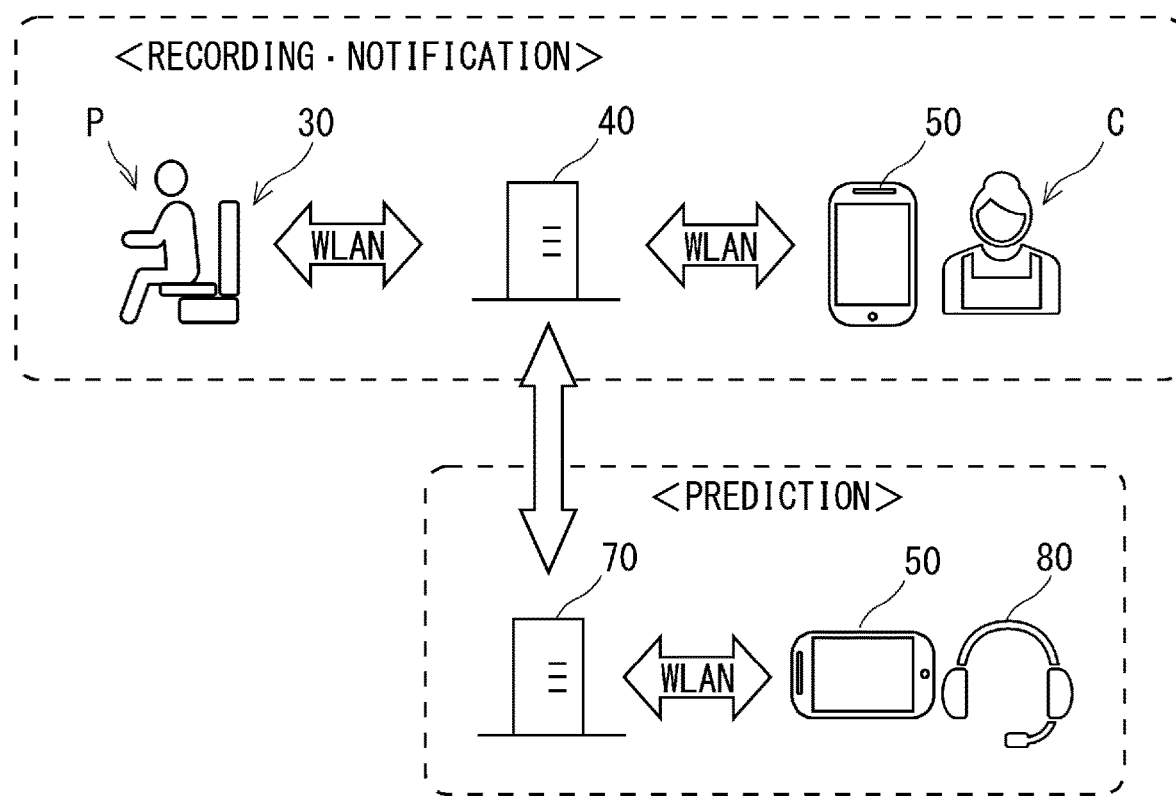
FIG. 10 is a conceptual diagram illustrating another example of the information processing system according to the second example embodiment.

Next, a system in which servers are distributed and processing examples in the system will be described with reference to FIG. 10 and FIG. 11 together with the aforementioned example of the excretion diary. FIG. 10 is a conceptual diagram illustrating another example of the information processing system according to the present example embodiment, and is a diagram illustrating an example of a system in which servers are distributed. FIG. 11 is a diagram illustrating an example of information recorded in the information processing system in FIG. 10.

The information processing system illustrated in FIG. 10 includes a toilet bowl 30 with the information processing apparatus 10, the server 40, and the terminal apparatus 50 for recording and notification, and also includes a server 70 for prediction. That is, the information processing system illustrated in FIG. 10 is a system in which functions are distributed by providing the prediction function among the functions of the server 40 in the aforementioned example to the server 70. It is assumed that the server 40 in FIG. 10 has a function of recording excretion information and an excretion diary generated on the basis of the excretion information, and the like.

The server 40 receives information, which is collected for a user P by the information processing apparatus 10 and the like in a toilet, via a wireless LAN, and records the received information as excretion information for the user P. As illustrated in FIG. 11, the excretion information may include, for example, the date and time of occurrence, a target person, the place of occurrence, the type of a subject (mainly, the type of excrement), the amount of urination, the shape of defecation, the color of defecation, a defecation count, a urination count, and special notes. Furthermore, the excretion information may also include the amount of defecation, and may also include a caregiver name (or caregiver ID) when there is a caregiver. The special notes may be input separately from the terminal apparatus 50 and the like. This example is also the same for the present system illustrated in FIG. 2. Furthermore, it is desirable that the excretion information is recorded in a database form.

Furthermore, the excretion information recorded in this way may be used as data for constructing a learned model, and except in the case of overfitting, it can be basically said that the accuracy of the learned model may be improved as the amount of data increases. Of course, the learned model in the present system and the like can be said to be a learning model to be operated, and when it is operated while learning, the learning model is also included in the concept.

Furthermore, the server 40 notifies a terminal apparatus 50 used by an observer C of the user P of presentation information based on the excretion information. Moreover, on the basis of the excretion information, the server 40 may generate an excretion diary as at least a part of the presentation information. The format of the excretion diary is not limited, but an example thereof will be described below. Furthermore, the server 40 may also output a print job (print data) for printing a target excretion diary to, for example, a printing apparatus (not illustrated) according to a print command from the terminal apparatus 50 and the like.

The server 40 may also calculate a urine flow rate (average value, maximum value, and the like) or the amount of urination (per time or per unit time) on the basis of the excretion information, and generate information, which indicates a reduction in the urine flow rate or the amount of urination, as at least a part of the presentation information. Actually, in imaging data at the time of urination, stagnant water is not only colored, but also stagnant water in a state where the water is temporarily increased or wavy is included as a subject. Thus, there is a difference in imaging data before urination and during or after urination, and information such as the amount of urination may be output as information of the learned model having reflected such a difference. Of course, even when the learned model is not used as mentioned in the first example embodiment, it is possible to acquire information such as the amount of urination by acquiring the above difference by comparison. The unit of the urine flow rate and the amount of urination is not limited, but may be, for example, ml/sec and ml, respectively. Furthermore, for example, a reduction in the urine flow rate may be expressed by a rate and the like of reduction in each urination, and for example, information, which indicates the state of reduction, may be generated as information indicating whether a set threshold is exceeded.

Furthermore, the server 40 may calculate a defecation count or the amount of defecation per unit time on the basis of the excretion information, and generate information, which indicates a reduction in a defecation count, as at least a part of the presentation information. Actually, in imaging data at the time of defecation, at least feces are included as a subject. Thus, there is a difference in imaging data before defecation and during or after defecation, and information such as the amount of defecation may be output as information of the learned model having reflected such a difference. Of course, even when the learned model is not used as mentioned in the first example embodiment, it is possible to acquire information such as the amount of defecation by acquiring the above difference by comparison. The unit of the amount of defecation is not limited, but may be, for example, ml/sec or cm³. Furthermore, for example, a reduction in a defecation count and the amount of defecation may be expressed by a rate and the like of reduction in the frequency of defecation and the amount of defecation, and for example, information, which indicates the state of reduction, may be generated as information indicating whether a set threshold is exceeded. Although it is possible to use only one of these calculations for defecation and urination, it is desirable to use both of them.

Furthermore, the server 70 acquires the collected information or the information recorded as the excretion diary from the server 40, and predicts an excretion timing by extracting and analyzing the acquired information. The excretion timing may include a defecation timing and a urination timing, and may also include a constipation timing and a urination disorder timing acquired by adding a predetermined time from the respective timings. Then, the server 70 may transmit a notification to an associated terminal apparatus 50 upon the arrival of the excretion timing or at the predetermined time before the excretion timing.

Note that the notification destination may be, for example, a notification apparatus of a nurse call system, another terminal apparatus (for example, a personal handy-phone system (PHS)) that an observer has other than the terminal apparatus 50, an intercom 80, and the like. Furthermore, as described above, when a user of the toilet has a terminal apparatus, the terminal apparatus may also be included in the notification destination.

In the case of a facility such as a hospital, the server 40 may be installed in the facility, and in the case of personal use, the server 40 may be installed in a private house or an apartment house. In either case, the server 40 may also be a cloud server. The same also applies to the server 70, but the server 70 may be connected to a plurality of installed servers 40 and the number of servers 70 may be smaller than the number of servers 40.

Furthermore, a program of the terminal apparatus 50 may be executably incorporated in the terminal apparatus 50 as care software having a function of presenting presentation information. Furthermore, in addition to the presentation information, the terminal apparatus 50 may also directly receive and store information acquired on the toilet side of the information processing apparatus 10 and the like, and may also receive and store various information recorded by the servers 40 and 70 in the same manner.

Next, various examples of the excretion diary will be described with reference to FIG. 12 to FIG. 15 by taking, as an example, a case where a user is a care receiver and an observer is a caregiver.

FIG. 12 is a diagram illustrating an example of a daily excretion diary for a certain person, which is generated in the information processing system in FIG. 2 or FIG. 10. The excretion diary illustrated in FIG. 12 is a daily diary specified by individual (Mr. PA in this example) and day, and includes time on a vertical axis, and a facility name, type, the amount, shape, and color of urine and feces, the excretion count, a caregiver name, and special notes on a horizontal axis. The terminal apparatus 50 may read the excretion diary having such a format from the server 40 by designating a toilet user and the date, and display the excretion diary.

FIG. 13 is a diagram illustrating an example of an excretion diary for a certain person, which is generated in the information processing system in FIG. 2 or FIG. 10, and FIG. 14 is a diagram illustrating a continuation of the excretion diary in FIG. 13. The excretion diary illustrated in FIG. 13 and FIG. 14 is a one-week diary specified by individual (Mr. PA in this example) and week, and includes time on a vertical axis, and the type, amount, shape, and color of urine and feces, the excretion count, and special notes on a horizontal axis. The terminal apparatus 50 may read the excretion diary having such a format from the server 40 by designating a toilet user and week, and display the excretion diary.

FIG. 15 is a diagram illustrating an example of a daily excretion diary for a plurality of persons, which is generated in the information processing system in FIG. 2 or FIG. 10. The excretion diary illustrated in FIG. 15 is a daily diary specified by a plurality of individuals (Mr. PA, Mr. PB, and Mr. PC in this example) and day, and includes time on a vertical axis, and the type, amount, shape, and color of urine and feces, the excretion count, and special notes on a horizontal axis. The terminal apparatus 50 may read the excretion diary having such a format from the server 40 by designating a plurality of toilet users and date, and display the excretion diary.

Furthermore, the server 40 may be configured to be able to switch and output these excretion diaries in response to a display switching command from the terminal apparatus 50.

With the above configuration, in the present system such as the information processing system in FIG. 10, it is possible to easily browse information for assisting a user of the toilet and browse the excretion diary (and add information) from the terminal apparatus 50. Of course, it is also possible to record and display information in a format other than the excretion diary illustrated in the above.

Figure 16:
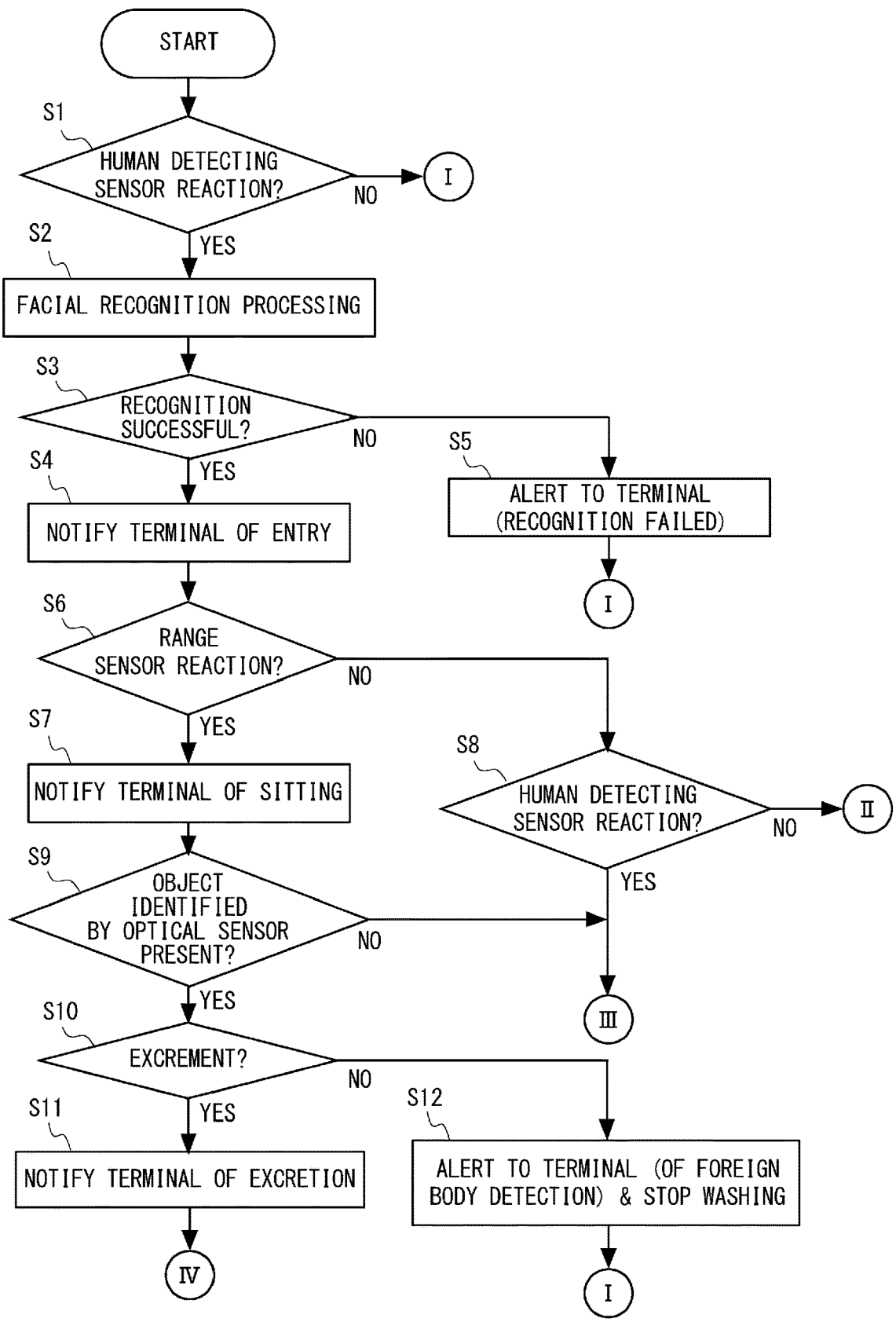
FIG. 16 is a flowchart for explaining an example of a process in the information processing system in FIG. 2 or FIG. 10.

Next, processing examples of the information processing system in FIG. 2 or FIG. 10 will be described with reference to FIG. 16 to FIG. 19 by taking, as an example, a case where a user is a care receiver and an observer is a caregiver. FIG. 16 is a flowchart for explaining an example of a process in the information processing system in FIG. 2 or FIG. 10, and FIG. 17 is a flowchart subsequent to FIG. 16.

Figure 17:
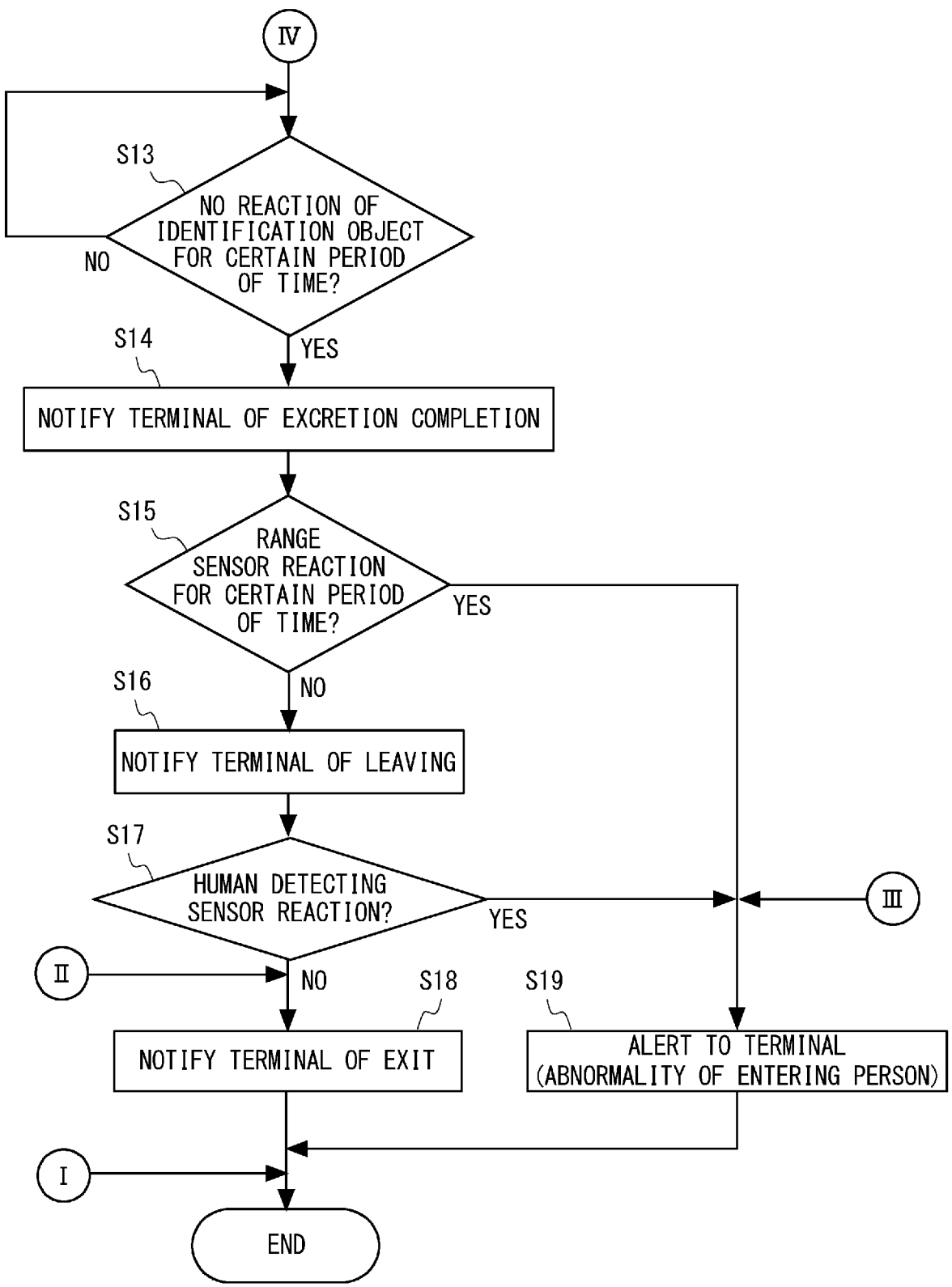
FIG. 17 is a flowchart subsequent to FIG. 16.

The process illustrated in FIG. 16 and FIG. 17 is an example of a process for recording, notification, and excretion prediction performed before a care receiver exits the toilet after entering the toilet and excreting. The process in the information processing system 10 is mainly performed by the CPU 11*a*, and the process of the server 40 (and the server 70) is mainly performed by the control unit thereof. Furthermore, in the process illustrated below may be performed for each excretion behavior and the like by being repeated as appropriate after completion.

First, the server 40 checks whether there is a reaction of the human detecting sensor 15*a*, which is transmitted from the information processing system 10 (step S1), and ends the process without notification when there is no reaction (in the case of NO). When the care receiver enters the toilet, the human detecting sensor 15a reacts and the check result is YES in step S1. In such a case, the information processing system 10 receives face image data captured by the second camera 15b and transmits the face image data to the server 40. The server 40 performs a facial recognition process (step S2). The server 40 checks whether the care receiver has been registered in the list of registered persons, and determines whether the recognition is successful (step S3). Note that the server 40 returns the determination result to the information processing system 10 side regardless of whether the recognition is successful.

In the case of YES in step S3 (when the care receiver is a registered person), the server 40 notifies the terminal apparatus 50 of entry (step S4). In the case of NO in step S3 (when the care receiver is an unregistered person), the server 40 notifies the terminal apparatus 50 of an alert indicating that the care receiver is an unregistered person (step S5), and ends the process. By the alert indicating that the care receiver is an unregistered person, a holder of the terminal apparatus 50 may ascertain the possibility that the care receiver is a suspicious person, for example.

Subsequent to step S4, the server 40 checks whether there is a reaction of the range sensor 16a, which is transmitted from the information processing system 10 (step S6), and notifies the terminal apparatus 50 of sitting (step S7) when there is a reaction (in the case of YES). In the case of NO in step S6 (when there is no reaction), the server 40 checks whether there is a reaction of the human detecting sensor 15a, which is transmitted from the information processing system 10 (step S8).

When there is no reaction of the human detecting sensor 15a (No in step S8), the server 40 notifies the terminal apparatus 50 of exit (step S18), and ends the process. When there is a reaction of the human detecting sensor 15a (YES in step S8), the server 40 notifies the terminal apparatus 50 of alert information indicating an abnormality of an entering person as illustrated in the presentation information 61 in FIG. 9 (step S19). The alert information is notified because any abnormality may occur in the care receiver in the toilet. After the process of step S19, the process ends.

Subsequent to step S7, the server 40 performs a subject identification process from imaging data acquired by the first camera 16b, which is transmitted from the information processing system 10, and determines whether an identifiable object is present (step S9). In the case of NO in step S9 (that is, when no subject is reflected), the server 40 proceeds to step S19 because any abnormality may occur in the care receiver in the toilet, and issues an alert.

In the case of YES in step S9, the server 40 determines whether the subject is excrement (foreign body) (step S10). In the case of YES in step S10 (when the subject is excrement), the server 40 notifies the terminal apparatus 50 of excretion (step S11).

On the other hand, in the case of NO in step S10 (when the subject is not excrement), there is a possibility that a foreign body has been dropped into the toilet. Thus, in such a case, the server 40 notifies the terminal apparatus 50 of alert information for notifying the detection of the foreign body as illustrated in the presentation information 63 in FIG. 9, and instructs the information processing system 10 to issue a command for stopping the washing function of the toilet bowl 20 (step S12). With this, the washing function is stopped, and the caregiver can go to the installation place of the toilet bowl 20 to remove the foreign body, can not only prevent a foreign body from entering a drain pipe, but also can hand over the foreign body to an inspection agency when the foreign body needs to be inspected. After the process of step S12, the process ends.

Subsequent to step S11, the server 40 determines whether an identification object (excrement or foreign body) has not been detected for a certain period of time, on the basis of imaging data transmitted from the information processing system 10 (step S13). When there is no reaction (in the case of YES), the server 40 notifies the terminal apparatus 50 of the completion of excretion (step S14). In the case of NO in step S13 (when the reaction continues), the server 40 waits until YES in step S13.

Subsequent to step S14, the server 40 checks whether there is a reaction of the range sensor 16a, which is transmitted from the information processing system 10, for a certain period of time (step S15). When the reaction state has elapsed for a certain period of time (YES in step S15), since the care receiver is sitting for a long time, there is a possibility that any abnormality may occur in the care receiver. Therefore, in such a case, the server 40 proceeds to step S19, notifies the terminal apparatus 50 of an alert, and ends the process. When there is no reaction of the range sensor 16a for a certain period of time (NO in step S15), the server 40 notifies the terminal apparatus 50 of leaving (that is, standing up) (step S16).

Subsequent to step S16, the server 40 checks whether there is a reaction of the human detecting sensor 15a, which is transmitted from the information processing system 10 (step S17). When there is no reaction of the human detecting sensor 15a (NO in step S17), the server 40 proceeds to step S18, notifies the terminal apparatus 50 of exit, and ends the process. When there is a reaction of the human detecting sensor 15a (YES in step S17), the server 40 proceeds to step S19, notifies the terminal apparatus 50 of alert information indicating an abnormality of the entering person, and ends the process.

Figure 18:
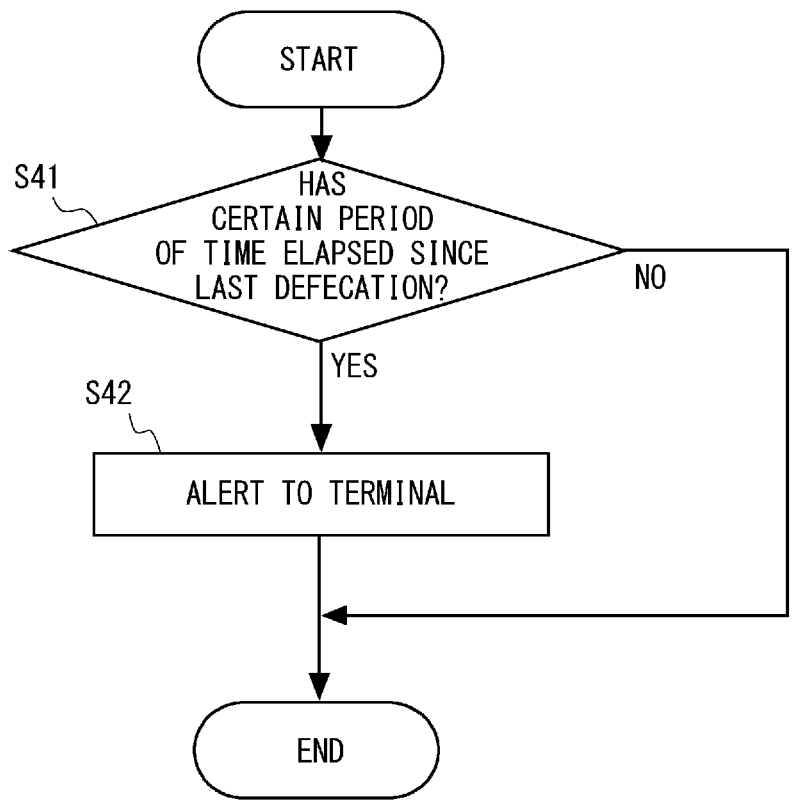
FIG. 18 is a flowchart for explaining an example of a defecation promotion process in the information processing system in FIG. 2 or FIG. 10.

An example of a defecation promotion process will be described with reference to FIG. 18. FIG. 18 is a flowchart for explaining an example of a defecation promotion process in the information processing system in FIG. 2 or FIG. 10. Hereinafter, an example mainly processed by the server 40 in FIG. 10 will be described.

The server 40 refers to recorded excretion information for each user, for example, the recording time of defecation identified by the first camera 16b, and determines whether a certain period of time (threshold with respect to time) has elapsed without defecation (step S41). It is preferable that the threshold is set to be changeable as appropriate and is also set to be changeable for each user. In the case of NO in step S41, the server 40 ends the process, and in the case of YES in step S41, the server 40 notifies the terminal apparatus 50 of alert information indicating that a certain period of time has elapsed without defecation (step S42) and ends the process. In such an example, as the simplest example, the excretion timing is set to a timing when a certain period of time has elapsed from previous defecation; however, the present disclosure is not limited thereto.

Figure 19:
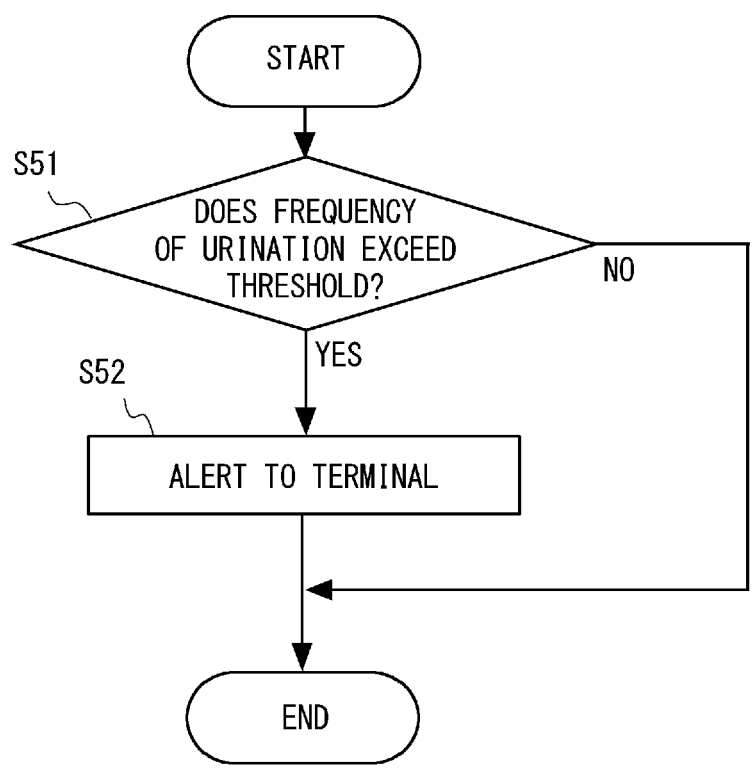
FIG. 19 is a flowchart for explaining an example of an alert process regarding a urination interval in the information processing system in FIG. 2 or FIG. 10.

An example of a urination interval alert process will be described with reference to FIG. 19. FIG. 19 is a flowchart for explaining an example of an alert process regarding a urination interval in the information processing system in FIG. 2 or FIG. 10.

The server 40 refers to recorded excretion information for each user, for example, the recording time of urination identified by the first camera 16b, and determines whether an interval at which urination is performed is smaller than a certain period of time (threshold with respect to time) (step S45). It is preferable that the threshold is set to be changeable as appropriate and is also set to be changeable for each user. In the case of NO in step S51, the server 40 ends the process, and in the case of YES in step S51, the server 40 notifies the terminal apparatus 50 of alert information indicating that the interval at which urination is performed is smaller than the certain period of time (step S52) and ends the process. In such an example, it is determined that urination is reduced when the state of reduction in urination has elapsed from previous defecation for a certain period of time; however, the present disclosure is not limited thereto.

As described above, the present system may achieve the effects described in the first example embodiment. Particularly, the present system has the following effects, for example.

According to the first effect, by automatically recording the content of excrement identified by a combination of the first camera and the machine learning, it is possible to eliminate the need for manual listening to excrement, measurement of the amount of urination, confirmation of feces, and generation of an excretion diary, which has been carried out so far. Particularly, in excretion assistance to care receivers, observation for generating an excretion diary may not be possible, and a care receiver who needs assistance may continue to sit on a toilet seat in a toilet because the care receiver is not able to notify a caregiver of the end of excretion by himself/herself after the end of excretion. However, such a situation can be prevented. With this, it is possible to reduce the work time of an observer such as a caregiver.

According to the second effect, when the first camera identifies an object other than excrement, an alert is notified to an observer and a washing function is stopped, thus it is possible to prevent an accident in which a solid body such as a urine absorbing pad is flushed to the drain pipe of the toilet. With this, it is possible to reduce the maintenance cost by eliminating the need for drain pipe construction by a contractor, which has been carried out so far.

According to the third effect, even when a care receiver is in a dangerous state in the toilet, it is possible to remotely ascertain such a dangerous state by information on person recognition by a facial recognition process by the range sensor, the human detecting sensor, and the second camera or an identification process by a Bluetooth tag and the like. Thus, the work of an observer to monitor the care receiver in front of the toilet, which has been carried out so far, becomes unnecessary, thus it is possible to reduce the excretion assistance time of the observer.

According to the fourth effect, it is possible to ascertain the possibility of constipation or urination disorder from information recording the content of excrement identified by the first camera (for example, it is storable as information in a database format). Thus, it is possible to reduce the cost of medicine by eliminating the need for administering a laxative even though listening about the presence or absence of feces, which has been carried out so far, is not necessary in consideration of safety because it is unreliable. Furthermore, a terminal apparatus held by a user of the toilet is also notified, thus it is possible to ascertain the tendency of urination disorder and the like and promote early consultation.

According to the fifth effect, it is possible to individually ascertain a urination interval from information recording the content of excrement identified by the first camera. Thus, since a care receiver does not have to use a diaper and a urine absorbing pad regularly, the cost can be reduced, and an observer may ascertain the condition of each care receiver and easily support the independence of each care receiver.

According to the sixth effect, it is possible to identify a user of the toilet by face image data captured by the range sensor, the human detecting sensor, and the second camera. Thus, when a caregiver is absent, an observer can be notified of entering the toilet alone, exiting the toilet alone, sitting on the toilet seat alone, leaving the toilet seat alone, and long-time sitting alone. By such a notification, the observer such as a caregiver can perform other tasks in parallel while assisting a care receiver in the toilet, thus it is possible to improve the efficiency of caregiving work.

According to the seventh effect, by individually selecting the display or non-display of various notifications, a caregiver can delete unnecessary notifications and display only necessary notifications, which makes it possible to reduce oversight of notifications and improve the efficiency of caregiving work.

Other Example Embodiments

[a]

In each example embodiment, the information processing system and functions of respective apparatuses included in the system have been described, but each apparatus is not limited to the illustrated configuration example and these functions may be implemented as the respective apparatuses.

[b]

Figure 20:
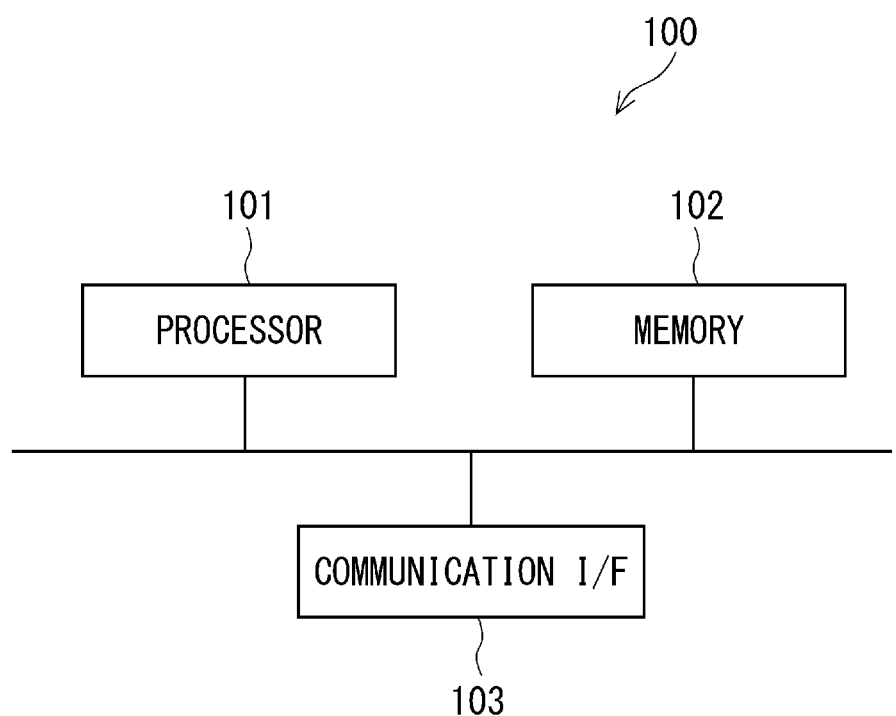
FIG. 20 is a diagram illustrating an example of a hardware configuration of an apparatus.

Each apparatus according to the first and second example embodiments may have the following hardware configuration. FIG. 20 is a diagram illustrating an example of a hardware configuration of the apparatus. The same also applies to the above another example embodiment [a].

An apparatus 100 illustrated in FIG. 20 may have a processor 101, a memory 102, and a communication interface (I/F) 103. The processor 101 may be, for example, a microprocessor, a microprocessor unit (MPU), a CPU, and the like. The processor 101 may also include a plurality of processors. The memory 102 is composed of, for example, a combination of a volatile memory and a nonvolatile memory. The functions of the respective apparatuses described in the first and second example embodiments are implemented by the processor 101 that reads and executes the program stored in the memory 102. At this time, the transmission/reception of information with another apparatus may be performed via the communication I/F 103 or an input/output interface (not illustrated).

In the aforementioned examples, the program may be stored using various types of non-transitory computer-readable mediums, and may be supplied to a computer. The non-transitory computer-readable medium includes various types of tangible storage mediums. Examples of the non-transitory computer-readable medium include a magnetic recording medium (for example, a flexible disk, a magnetic tape, a hard disk drive), and a magneto-optical recording medium (for example, a magneto-optical disk). Moreover, this example includes a CD-ROM (Read Only Memory), a CD-R, and a CD-R/W. Moreover, this example includes a semiconductor memory (for example, a mask ROM, a programmable ROM (PROM), an erasable PROM (EPROM), a flash ROM, a random access memory (RAM)). Furthermore, the program may also be supplied to the computer by various types of transitory computer-readable mediums. Examples of the transitory computer-readable medium include an electrical signal, an optical signal, and an electromagnetic wave. The transitory computer-readable medium may supply the program to the computer via a wired communication path such as an electric wire and an optical fiber or a wireless communication path.

[c]

Moreover, in the aforementioned each example embodiment, as illustrated by exemplifying the procedure of an information processing method in the information processing apparatus, the present disclosure may also take the form of the information processing method. The information processing method may include the following acquisition step, generation step, output step, and washing control step. In the acquisition step, excretion information indicating content of excretion is acquired on the basis of imaging data captured by an image capture apparatus installed to include in an image capture range an excretion range of excrement in a toilet bowl of a toilet. In the generation step, presentation information is generated on the basis of the excretion information. In the output step, the presentation information is output. In the washing control step, a washing function of the toilet bowl is controlled. Moreover, in the acquisition step, information, which indicates whether a foreign body that is an object other than feces and urine is included in the imaging data captured by the image capture apparatus as a subject excluding the toilet bowl and washing liquid for the toilet bowl, is acquired as at least a part of the excretion information. Furthermore, in the washing control step, when information including the foreign body is acquired as the excretion information in the acquisition step, a stop command for stopping the washing function is output to the toilet bowl side. Furthermore, in the generation step, when the information including the foreign body is acquired as the excretion information in the acquisition step, alert information is generated as at least a part of the presentation information. Other examples are as described in the aforementioned each example embodiment. Furthermore, it can be said that the above program is a program for causing the information processing apparatus (computer) to perform the acquisition step, the generation step, the output step, and the washing control step.

[d]

Moreover, the aforementioned various example embodiments are premised on performing washing control, acquiring information on whether there is a foreign body, and stopping a washing function on the basis of the information; the present disclosure does not exclude an information processing system, an information processing apparatus, an information processing method, and a program, which do not include these processes and functions.

The present disclosure is not limited to the aforementioned example embodiments, and can be appropriately changed without departing from the spirit. Furthermore, the present disclosure may also be embodied by appropriately combining the respective example embodiments.

Some or all of the aforementioned example embodiments may also be described in the following supplementary notes, but are not limited thereto.

Supplementary Notes

Supplementary Note 1

An information processing system comprising:
an acquisition unit for acquiring excretion information indicating a content of excretion, based on imaging data captured by an image capture apparatus installed in such a way as to include, in an image capture range, an excretion range of excrement in a toilet bowl of a toilet;
a generation unit for generating presentation information, based on the excretion information;
an output unit for outputting the presentation information; and
a washing control unit for controlling a washing function of the toilet bowl, wherein
the acquisition unit acquires information that indicates whether a foreign body being an object other than feces and urine is included in the imaging data captured by the image capture apparatus as a subject excluding the toilet bowl and washing liquid for the toilet bowl, as at least a part of the excretion information,
the washing control unit outputs a stop command for stopping the washing function to a side of the toilet bowl when the acquisition unit acquires information including the foreign body as the excretion information, and
the generation unit generates alert information as at least a part of the presentation information when the acquisition unit acquires the information including the foreign body as the excretion information.

Supplementary Note 2

The information processing system according to Supplementary note 1, wherein the acquisition unit acquires the excretion information by using a learned model that outputs the excretion information, based on the imaging data captured by the image capture apparatus.

Supplementary Note 3

The information processing system according to Supplementary note 1, wherein the acquisition unit and the generation unit acquire the excretion information and the presentation information by using a learned model that outputs the excretion information and the presentation information, based on the imaging data captured by the image capture apparatus.

Supplementary Note 4

The information processing system according to any one of Supplementary notes 1 to 3, wherein the generation unit generates an excretion diary as a part of the presentation information, based on the excretion information.

Supplementary Note 5

The information processing system according to any one of Supplementary notes 1 to 4, wherein the generation unit calculates a urine flow rate or an amount of urination, based on the excretion information, and generates information that indicates a reduction state in the urine flow rate or the amount of urination, as at least a part of the presentation information.

Supplementary Note 6

The information processing system according to any one of Supplementary notes 1 to 5, wherein the generation unit calculates a defecation count or an amount of defecation per unit time, based on the excretion information, and generates information that indicates a reduction state in the defecation count, as at least a part of the presentation information.

Supplementary Note 7

The information processing system according to any one of Supplementary notes 1 to 6, wherein the generation unit calculates an excretion timing, based on the excretion information and a date and time of an excretion behavior, and generates information for notifying the excretion timing as at least a part of the presentation information.

Supplementary Note 8

The information processing system according to any one of Supplementary notes 1 to 7, wherein the acquisition unit collects the imaging data for a plurality of toilets and acquires the excretion information.

Supplementary Note 9

The information processing system according to any one of Supplementary notes 1 to 8, wherein the generation unit generates the presentation information for each user, based on identification data for identifying a user of the toilet bowl.

Supplementary Note 10

The information processing system according to Supplementary note 9, wherein the generation unit generates the presentation information for each user, based on the identification data and entry/exit data recording entry/exit to/from a toilet in which the toilet bowl is installed.

Supplementary Note 11

The information processing system according to Supplementary note 9 or 10, wherein the identification data are data identifying a user by performing facial recognition processing, based on face image data being captured by another image capture apparatus installed in such a way as to include a face of a user in an image capture range, in the toilet bowl or a room in which the toilet bowl is installed.

Supplementary Note 12

The information processing system according to Supplementary note 11, further comprising the another image capture apparatus.

Supplementary Note 13

The information processing system according to any one of Supplementary notes 1 to 12, further comprising the image capture apparatus.

Supplementary Note 14

An information processing apparatus comprising an image capture apparatus and being installed on a toilet bowl of a toilet in such a way that the image capture apparatus is disposed in such a way as to include, in an image capture range, an excretion range of excrement in the toilet bowl, the information processing apparatus further comprising:
an acquisition unit for acquiring excretion information indicating a content of excretion, based on imaging data captured by the image capture apparatus;
a generation unit for generating presentation information, based on the excretion information;
an output unit for outputting the presentation information; and
a washing control unit for controlling a washing function of the toilet bowl, wherein the acquisition unit acquires information that indicates whether a foreign body being an object other than feces and urine is included in the imaging data captured by the image capture apparatus as a subject excluding the toilet bowl and washing liquid for the toilet bowl, as at least a part of the excretion information,
the washing control unit outputs a stop command for stopping the washing function to a side of the toilet bowl when the acquisition unit acquires information including the foreign body as the excretion information, and
the generation unit generates alert information as at least a part of the presentation information when the acquisition unit acquires the information including the foreign body as the excretion information.

Supplementary Note 15

An information processing method comprising:
an acquisition step of acquiring excretion information indicating a content of excretion, based on imaging data captured by an image capture apparatus installed in such a way as to include, in an image capture range, an excretion range of excrement in a toilet bowl of a toilet;
a generation step of generating presentation information, based on the excretion information;
an output step of outputting the presentation information; and
a washing control step of controlling a washing function of the toilet bowl, wherein:
in the acquisition step, information that indicates whether a foreign body being an object other than feces and urine is included in the imaging data captured by the image capture apparatus as a subject excluding the toilet bowl and washing liquid for the toilet bowl, is acquired as at least a part of the excretion information;
in the washing control step, when information including the foreign body is acquired as the excretion information in the acquisition step, a stop command for stopping the washing function is output to a side of the toilet bowl; and
in the generation step, when the information including the foreign body is acquired as the excretion information in the acquisition step, alert information is generated as at least a part of the presentation information.

Supplementary Note 16

A program causing a computer to perform:
an acquisition step of acquiring excretion information indicating a content of excretion, based on imaging data captured by an image capture apparatus installed in such a way as to include, in an image capture range, an excretion range of excrement in a toilet bowl of a toilet;
a generation step of generating presentation information, based on the excretion information;
an output step of outputting the presentation information; and
a washing control step of controlling a washing function of the toilet bowl, wherein:
in the acquisition step, information that indicates whether a foreign body being an object other than feces and urine is included in the imaging data captured by the image capture apparatus as a subject excluding the toilet bowl and washing liquid for the toilet bowl, is acquired as at least a part of the excretion information;

in the washing control step, when information including the foreign body is acquired as the excretion information in the acquisition step, a stop command for stopping the washing function is output to a side of the toilet bowl; and in the generation step, when the information including the foreign body is acquired as the excretion information in the acquisition step, alert information is generated as at least a part of the presentation information.

Although the present invention has been described with reference to the embodiments, the present invention is not limited to the above. Various changes that can be understood by those skilled in the art can be made in the configuration and details of the present invention within the scope of the invention.

This application claims priority based on Japanese Patent Application No. 2019-146294 filed on Aug. 8, 2019, the contents of which are incorporated herein by reference.

REFERENCE SIGNS LIST

1 INFORMATION PROCESSING SYSTEM
1a ACQUISITION UNIT
1b GENERATION UNIT
1c OUTPUT UNIT
1d WASHING CONTROL UNIT
10 INFORMATION PROCESSING APPARATUS
11 SECOND EXTERNAL BOX
11a CPU
11b CONNECTOR
11c, 11d USB I/F
12 INTER-BOX CONNECTION UNIT
13 FIRST EXTERNAL BOX
14a WiFi MODULE
14b BLUETOOTH MODULE
15a HUMAN DETECTING SENSOR
15b SECOND CAMERA
16a RANGE SENSOR
16b FIRST CAMERA
20 TOILET BOWL
21 BODY
22 TOILET SEAT
23 TOILET SEAT COVER
30 TOILET BOWL WITH INFORMATION PROCESSING APPARATUS
40, 70 SERVER
41 CONTROL UNIT
42 STORAGE UNIT
50 TERMINAL APPARATUS
51 DISPLAY SCREEN
52, 53, 54, 55, 56, 57, 58, 59, 61, 62, 63, 64 PRESENTATION INFORMATION
54a BUTTON
80 INTERCOM
100 APPARATUS
101 PROCESSOR
102 MEMORY
103 COMMUNICATION INTERFACE

What is claimed is:

1. An information processing system comprising:

an acquisition unit for acquiring excretion information indicating a content of excretion, based on imaging data captured by an image capture apparatus installed in such a way as to include, in an image capture range, an excretion range of excrement in a toilet bowl of a toilet;

a generation unit for generating presentation information, based on the excretion information;

an output unit for outputting the presentation information; and a washing control unit for controlling a washing function of the toilet bowl, wherein the acquisition unit acquires information that indicates whether a foreign body being an object other than feces and urine is included in the imaging data captured by the image capture apparatus as a subject excluding the toilet bowl and washing liquid for the toilet bowl, as at least a part of the excretion information, the washing control unit outputs a stop command for stopping the washing function to a side of the toilet bowl when the acquisition unit acquires information including the foreign body as the excretion information, and the generation unit generates alert information as at least a part of the presentation information when the acquisition unit acquires the information including the foreign body as the excretion information.

2. The information processing system according to claim 1, wherein the acquisition unit acquires the excretion information by using a learned model that outputs the excretion information, based on the imaging data captured by the image capture apparatus.

3. The information processing system according to claim 1, wherein the acquisition unit and the generation unit acquire the excretion information and the presentation information by using a learned model that outputs the excretion information and the presentation information, based on the imaging data captured by the image capture apparatus.

4. The information processing system according to claim 1, wherein the generation unit generates an excretion diary as a part of the presentation information, based on the excretion information.

5. The information processing system according to claim 1, wherein the generation unit calculates a urine flow rate or an amount of urination, based on the excretion information, and generates information that indicates a reduction state in the urine flow rate or the amount of urination, as at least a part of the presentation information.

6. The information processing system according to claim 1, wherein the generation unit calculates a defecation count or an amount of defecation per unit time, based on the excretion information, and generates information that indicates a reduction state in the defecation count, as at least a part of the presentation information.

7. The information processing system according to claim 1, wherein the generation unit calculates an excretion timing, based on the excretion information and a date and time of an excretion behavior, and generates information for notifying the excretion timing as at least a part of the presentation information.

8. The information processing system according to claim 1, wherein the acquisition unit collects the imaging data for a plurality of toilets and acquires the excretion information.

9. The information processing system according to claim 1, wherein the generation unit generates the presentation information for each user, based on identification data for identifying a user of the toilet bowl.

10. The information processing system according to claim 9, wherein the generation unit generates the presentation information for each user, based on the identification data and entry/exit data recording entry/exit to/from a toilet in which the toilet bowl is installed.

11. The information processing system according to claim 9, wherein the identification data are data identifying a user by performing facial recognition processing, based on face image data being captured by another image capture apparatus installed in such a way as to include a face of a user in an image capture range, in the toilet bowl or a room in which the toilet bowl is installed.

12. The information processing system according to claim 11, further comprising the another image capture apparatus.

13. The information processing system according to claim 1, further comprising the image capture apparatus.

14. An information processing method comprising:
  acquiring excretion information indicating a content of excretion, based on imaging data captured by an image capture apparatus installed in such a way as to include, in an image capture range, an excretion range of excrement in a toilet bowl of a toilet;
  generating presentation information, based on the excretion information;
  outputting the presentation information; and
  controlling a washing function of the toilet bowl, wherein:
  in the acquiring, information that indicates whether a foreign body being an object other than feces and urine is included in the imaging data captured by the image capture apparatus as a subject excluding the toilet bowl and washing liquid for the toilet bowl, is acquired as at least a part of the excretion information;
  in the controlling, when information including the foreign body is acquired as the excretion information in the acquiring, a stop command for stopping the washing function is output to a side of the toilet bowl; and
  in the generating, generation step, when the information including the foreign body is acquired as the excretion information in the acquiring, alert information is generated as at least a part of the presentation information.

15. A non-transitory computer-readable medium storing a program causing a computer to perform:
  acquiring excretion information indicating a content of excretion, based on imaging data captured by an image capture apparatus installed in such a way as to include, in an image capture range, an excretion range of excrement in a toilet bowl of a toilet;
  generating presentation information, based on the excretion information;
  outputting the presentation information; and
  controlling a washing function of the toilet bowl, wherein:
  in the acquiring, information that indicates whether a foreign body being an object other than feces and urine is included in the imaging data captured by the image capture apparatus as a subject excluding the toilet bowl and washing liquid for the toilet bowl, is acquired as at least a part of the excretion information;
  in the controlling, when information including the foreign body is acquired as the excretion information in the acquiring, a stop command for stopping the washing function is output to a side of the toilet bowl; and
  in the generating, when the information including the foreign body is acquired as the excretion information in the acquiring, alert information is generated as at least a part of the presentation information.

* * * * *